(12) United States Patent
Metzger et al.

(10) Patent No.: US 10,485,555 B2
(45) Date of Patent: Nov. 26, 2019

(54) BI-CRUCIATE KNEE SYSTEM

(71) Applicant: Biomet Manufacturing, LLC, Warsaw, IN (US)

(72) Inventors: Robert Metzger, Wakarusa, IN (US); Nathan Emick Belcher, Warsaw, IN (US); Audra C. Watson, Fort Wayne, IN (US); Bradley T. Durcholz, Warsaw, IN (US); Joshua B. Catanzarite, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 984 days.

(21) Appl. No.: 14/876,142

(22) Filed: Oct. 6, 2015

(65) Prior Publication Data

US 2016/0045205 A1 Feb. 18, 2016

Related U.S. Application Data

(63) Continuation of application No. 13/470,630, filed on May 14, 2012, now Pat. No. 9,161,761.
(Continued)

(51) Int. Cl.
*A61B 17/15* (2006.01)
*A61B 17/17* (2006.01)
(Continued)

(52) U.S. Cl.
CPC ........ *A61B 17/157* (2013.01); *A61B 17/1764* (2013.01); *A61F 2/461* (2013.01);
(Continued)

(58) Field of Classification Search
CPC . A61B 17/154; A61B 17/155; A61B 17/1764; A61B 17/157; A61F 2/461;
(Continued)

(56) References Cited

U.S. PATENT DOCUMENTS

D274,094 S 5/1984 Kenna
4,759,350 A * 7/1988 Dunn ................... A61B 17/154
606/82

(Continued)

FOREIGN PATENT DOCUMENTS

CN 102149337 A 8/2011
JP 2010504766 A 2/2010
(Continued)

OTHER PUBLICATIONS

"U.S. Appl. No. 13/470,630, 312 Amendment filed Sep. 10, 2015", 3 pgs.
(Continued)

*Primary Examiner* — David W Bates
*Assistant Examiner* — Marcela I Shirsat
(74) *Attorney, Agent, or Firm* — Schwegman Lundberg & Woessner, P.A.

(57) ABSTRACT

An instrument set and related method for preparing a proximal tibia during a bi-cruciate retaining procedure are disclosed. The instrument set can include a tibial resection block, a cut guide, and a locking arm. The tibial resection block can be configured to be fixed to an anterior portion of the proximal tibia. The tibial resection block can define a slot that extends in a medial-lateral direction when the tibial resection block is fixed to the proximal tibia. The cut guide can have a body, a medial arm, and a lateral arm. A medial cut slot can be defined between the body and the medial arm. A lateral cut slot can be defined between the body and the lateral arm. The cut guide can further comprise a tongue extending therefrom. The tongue can be configured to be received by and slidably translate along the slot of the tibial resection block.

19 Claims, 18 Drawing Sheets

Related U.S. Application Data

(60) Provisional application No. 61/486,023, filed on May 13, 2011, provisional application No. 61/593,521, filed on Feb. 1, 2012.

(51) Int. Cl.
*A61F 2/46* (2006.01)
*A61F 2/38* (2006.01)

(52) U.S. Cl.
CPC .......... *A61F 2/4637* (2013.01); *A61F 2/4657* (2013.01); *A61F 2/4684* (2013.01); *A61B 17/154* (2013.01); *A61F 2/389* (2013.01); *A61F 2/3859* (2013.01); *A61F 2002/4658* (2013.01); *A61F 2002/4661* (2013.01); *A61F 2002/4668* (2013.01); *A61F 2002/4681* (2013.01)

(58) Field of Classification Search
CPC .................. A61F 2/4657; A61F 2/4684; A61F 2002/4658; A61F 2002/4668
USPC .......... 600/214, 218–222; 269/3, 6, 95, 166, 269/246; 606/86 R–90, 96–98, 105, 606/54–59, 82
See application file for complete search history.

(56) References Cited

U.S. PATENT DOCUMENTS

| | | |
|---|---|---|
| 4,769,040 A | 9/1988 | Wevers |
| D326,156 S | 5/1992 | Martinez |
| 5,137,536 A | 8/1992 | Koshino |
| D346,218 S | 4/1994 | White |
| D346,979 S | 5/1994 | Stalcup et al. |
| 5,370,701 A | 12/1994 | Finn |
| D358,211 S | 5/1995 | Cohen |
| D358,647 S | 5/1995 | Cohen et al. |
| D369,863 S | 5/1996 | Hayes |
| D373,825 S | 9/1996 | Hayes |
| 5,681,316 A | 10/1997 | DeOrio et al. |
| 5,683,396 A | 11/1997 | Tokish et al. |
| 5,702,464 A * | 12/1997 | Lackey ................. A61F 2/4684 623/20.32 |
| 5,776,201 A | 7/1998 | Colleran et al. |
| 6,047,826 A | 4/2000 | Kalinski et al. |
| 6,126,692 A | 10/2000 | Robie et al. |
| 6,485,519 B2 | 11/2002 | Meyers et al. |
| 7,335,206 B2 | 2/2008 | Steffensmeier et al. |
| 7,569,060 B2 * | 8/2009 | Faoro ................. A61B 17/157 606/87 |
| 7,678,115 B2 | 3/2010 | D'alessio, II et al. |
| D626,234 S | 10/2010 | Otto et al. |
| 8,343,227 B2 | 1/2013 | Metzger et al. |
| D685,909 S | 7/2013 | Lomicka et al. |
| 8,715,359 B2 | 5/2014 | Deffenbaugh et al. |
| 8,728,167 B2 | 5/2014 | Collazo |
| 8,911,501 B2 | 12/2014 | Irwin et al. |
| D729,189 S | 5/2015 | Kangasmaa et al. |
| 9,161,761 B2 * | 10/2015 | Metzger ............... A61B 17/157 |
| 9,492,183 B2 * | 11/2016 | Wilkinson ........... A61B 17/157 |
| 2003/0130665 A1 * | 7/2003 | Pinczewski .......... A61B 17/154 606/88 |
| 2004/0138755 A1 | 7/2004 | O'connor et al. |
| 2004/0153162 A1 | 8/2004 | Sanford et al. |
| 2004/0167531 A1 | 8/2004 | Hodorek |
| 2004/0193280 A1 | 9/2004 | Webster et al. |
| 2005/0149042 A1 | 7/2005 | Metzger |
| 2006/0184176 A1 | 8/2006 | Straszheim-Morley et al. |
| 2008/0091273 A1 | 4/2008 | Hazebrouck |
| 2008/0215059 A1 | 9/2008 | Carignan et al. |
| 2009/0125114 A1 * | 5/2009 | May .................. A61B 17/1764 623/20.14 |
| 2009/0222014 A1 | 9/2009 | Bojarski et al. |
| 2010/0016980 A1 | 1/2010 | Donno et al. |
| 2010/0030571 A1 | 2/2010 | Jones et al. |
| 2010/0130665 A1 | 5/2010 | Beigbeder et al. |
| 2010/0298947 A1 | 11/2010 | Unger |
| 2010/0305575 A1 | 12/2010 | Wilkinson et al. |
| 2010/0305710 A1 | 12/2010 | Metzger |
| 2010/0305711 A1 * | 12/2010 | McKinnon ........... A61B 17/155 623/20.32 |
| 2010/0331848 A1 * | 12/2010 | Smith .................. A61B 17/155 606/88 |
| 2011/0040387 A1 | 2/2011 | Ries et al. |
| 2011/0190898 A1 | 8/2011 | Lenz et al. |
| 2012/0179266 A1 | 7/2012 | Collazo |
| 2012/0316563 A1 | 12/2012 | Metzger et al. |
| 2012/0330429 A1 | 12/2012 | Axelson, Jr. et al. |
| 2014/0066934 A1 | 3/2014 | Deirmengian et al. |
| 2014/0207196 A1 | 7/2014 | Slagle et al. |
| 2014/0243990 A1 | 8/2014 | Collazo et al. |
| 2014/0296859 A1 | 10/2014 | Claypool et al. |
| 2015/0173781 A1 | 6/2015 | Metzger et al. |

FOREIGN PATENT DOCUMENTS

| | | |
|---|---|---|
| JP | 2018507074 A | 3/2018 |
| WO | WO-9729696 A1 | 8/1997 |
| WO | WO 2008091358 A1 * | 7/2008 .......... A61B 17/157 |
| WO | WO-2008091358 A1 | 7/2008 |
| WO | WO-2010029333 A1 | 3/2010 |
| WO | WO-2010138832 A1 | 12/2010 |
| WO | WO-2012158604 A1 | 11/2012 |
| WO | WO-2013063386 A1 | 5/2013 |
| WO | WO-2016141274 A1 | 9/2016 |

OTHER PUBLICATIONS

"U.S. Appl. No. 13/470,630, Final Office Action dated Jul. 3, 2014", 14 pgs.

"U.S. Appl. No. 13/470,630, Non Final Action with Restriction Requirement dated Oct. 9, 2013", 7 pgs.

"U.S. Appl. No. 13/470,630, Non Final Office Action dated Nov. 21, 2013", 11 pgs.

"U.S. Appl. No. 13/470,630, Non Final Office Action dated Dec. 18, 2014", 15 pgs.

"U.S. Appl. No. 13/470,630, Notice of Allowance dated Jun. 25, 2015", 9 pgs.

"U.S. Appl. No. 13/470,630, PTO Response to Rule 312 Communication dated Sep. 14, 2015", 2 pgs.

"U.S. Appl. No. 13/470,630, Response filed Feb. 21, 2014 to Non Final Office Action dated Nov. 21, 2013", 12 pgs.

"U.S. Appl. No. 13/470,630, Response filed Mar. 16, 2015 to Non Final Office Action dated Dec. 18, 2014", 16 pgs.

"U.S. Appl. No. 13/470,630, Response filed Sep. 29, 2014 to Final Office Action dated Jul. 3, 2014", 14 pgs.

"U.S. Appl. No. 13/470,630, Response filed Nov. 8, 2013 to Non Final Action with Restriction Requirement dated Oct. 9, 2013", 2 pgs.

"U.S. Appl. No. 13/470,630, Supplemental Response filed Mar. 17, 2015 to Non Final Office Action dated Dec. 18, 2014", 16 pgs.

"U.S. Appl. No. 14/013,859, Restriction Requirement dated Aug. 25, 2016", 7 pgs.

"U.S. Appl. No. 29/484,228, Final Office Action dated Feb. 12, 2015", 7 pgs.

"U.S. Appl. No. 29/484,228, Non Final Office Action dated Sep. 30, 2014", 10 pgs.

"U.S. Appl. No. 29/484,228, Response filed Jan. 30, 2015 to Non Final Office Action dated Sep. 30, 2014", 6 pgs.

"U.S. Appl. No. 29/484,236, Non Final Office Action dated Jun. 3, 2015", 11 pgs.

"Australian Application Serial No. 2012256057, First Examiner Report dated Dec. 1, 2015", 2 pgs.

"Australian Application Serial No. 2012256057, Response filed Apr. 6, 2016 to First Examiner Report dated Dec. 1, 2015", 6 pgs.

"International Application Serial No. PCT/US2012/037750, International Preliminary Report on Patentability dated Nov. 28, 2013", 9 pgs.

(56) References Cited

OTHER PUBLICATIONS

"International Application Serial No. PCT/US2012/037750, International Search Report dated Jul. 4, 2012", 6 pgs.
"International Application Serial No. PCT/US2012/037750, Written Opinion dated Jul. 4, 2012", 7 pgs.
"International Application Serial No. PCT/US2016/020836 International Search Report dated Jul. 8, 2016", 6 pgs.
"International Application Serial No. PCT/US2016/020836 Written Opinion dated Jul. 8, 2016", 11 pgs.
"International Application Serial No. PCT/US2016/020836, Invitation to Pay Additional Fees and Partial Search Report dated May 11, 2016", 8 pgs.
"Japanese Application Serial No. 2014-511440, Office Action dated Apr. 15, 2016", 7 pgs.
"Japanese Application Serial No. 2014-511440, Response filed Jul. 13, 2016 to Office Action dated Apr. 15, 2016", 9 pgs.
"U.S. Appl. No. 14/013,859, Response filed Jan. 9, 2018 to Non Final Office Action dated Sep. 21, 2017", 12 pgs.
"U.S. Appl. No. 14/639,522, Response filed Dec. 4, 2017 to Restriction Requirement dated Oct. 5, 2017", 8 pgs.
"Australian Application Serial No. 2016210631, Response filed Nov. 22, 2017 to First Examination Report dated Sep. 30, 2017", 18 pgs.
"U.S. Appl. No. 14/013,859 Response filed Feb. 9, 2017 to Non Final Office Action dated Nov. 23, 2016", 10 pgs.
"U.S. Appl. No. 14/013,859, Final Office Action dated May 22, 2017", 11 pgs.
"U.S. Appl. No. 14/013,859, Non Final Office Action dated Sep. 21, 2017", 15 pgs.
"U.S. Appl. No. 14/013,859, Non Final Office Action dated Nov. 23, 2016", 11 pgs.
"U.S. Appl. No. 14/013,859, Response filed Aug. 21, 2017 to Final Office Action dated May 22, 2017", 12 pgs.
"U.S. Appl. No. 14/013,859, Response filed Oct. 5, 2016 to Restriction Requirement dated Aug. 25, 2016", 8 pgs.
"U.S. Appl. No. 14/639,522, Restriction Requirement dated Oct. 5, 2017", 8 pgs.
"Australian Application Serial No. 2016210631, First Examination Report dated Sep. 30, 2017", 7 pgs.
"International Application Serial No. PCT/US2016/020836, International Preliminary Report on Patentability dated Sep. 14, 2017", 12 pgs.
"U.S. Appl. No. 14/639,522, Non Final Office Action dated Mar. 7, 2018", 21 pgs.
"U.S. Appl. No. 14/639,522, Final Office Action dated Sep. 27, 2018", 21 pgs.
"U.S. Appl. No. 14/639,522, Response filed Jun. 6, 2018 to Non Final Office Action dated Mar. 7, 2018", 15 pgs.
"U.S. Appl. No. 14/639,522, Response filed Nov. 21, 2018 to Final Office action dated Sep. 27, 2018", 16 pgs.
"Chinese Application Serial No. 201680024942.0, Office Action dated Oct. 9, 2018", (W/ English Translation of Claims), 7 pgs.
"European Application Serial No. 16710584.0, Response filed May 21, 2018 to Office Action dated Nov. 10, 2017", 15 pgs.
"U.S. Appl. No. 14/639,522, Advisory Action dated Dec. 21, 2018", 3 pgs.
"U.S. Appl. No. 14/639,522, Response filed Jan. 14, 2019 to Advisory Action dated Dec. 21, 2018", 12 pgs.
"U.S. Appl. No. 16/419,459, Preliminary Amendment filed May 23, 2019", 7 pgs.
"Chinese Application Serial No. 201680024942.0, Response filed Jan. 10, 2019 to Office Action dated Oct. 9, 2018", (W/ English Claims), 7 pgs.

* cited by examiner

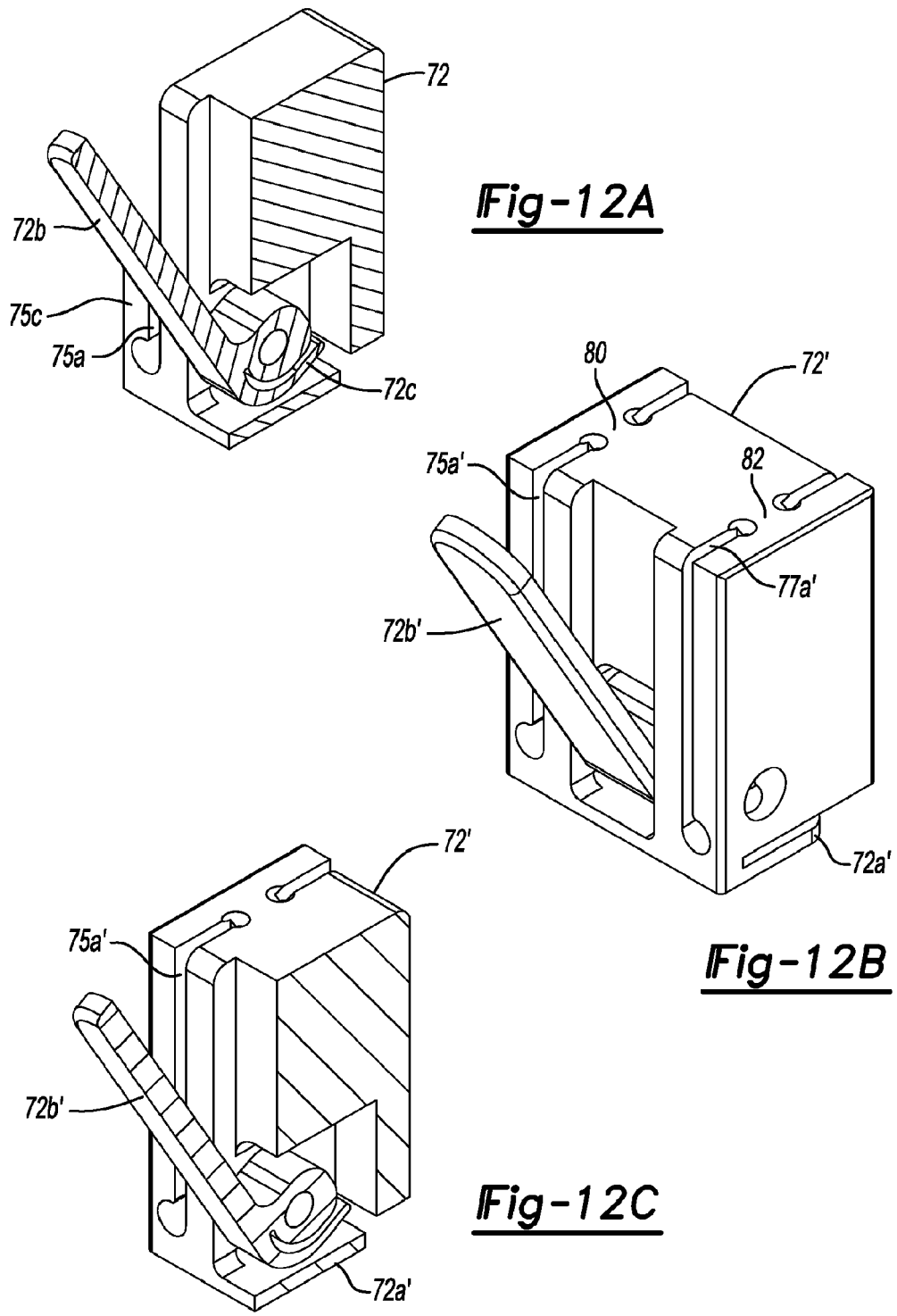

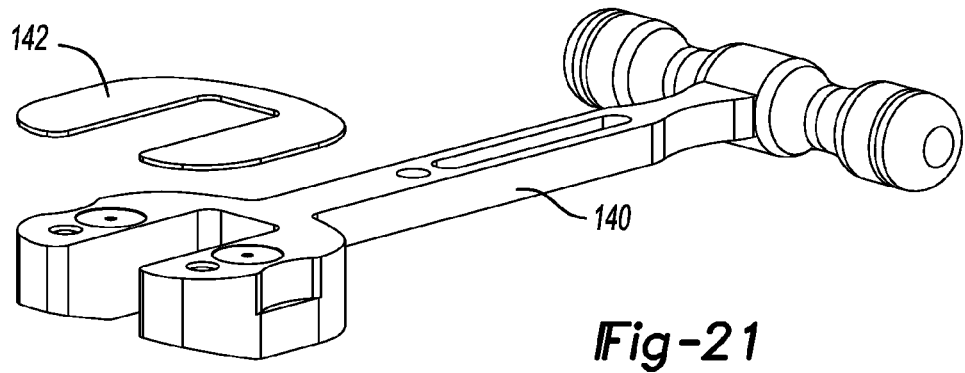
Fig-21
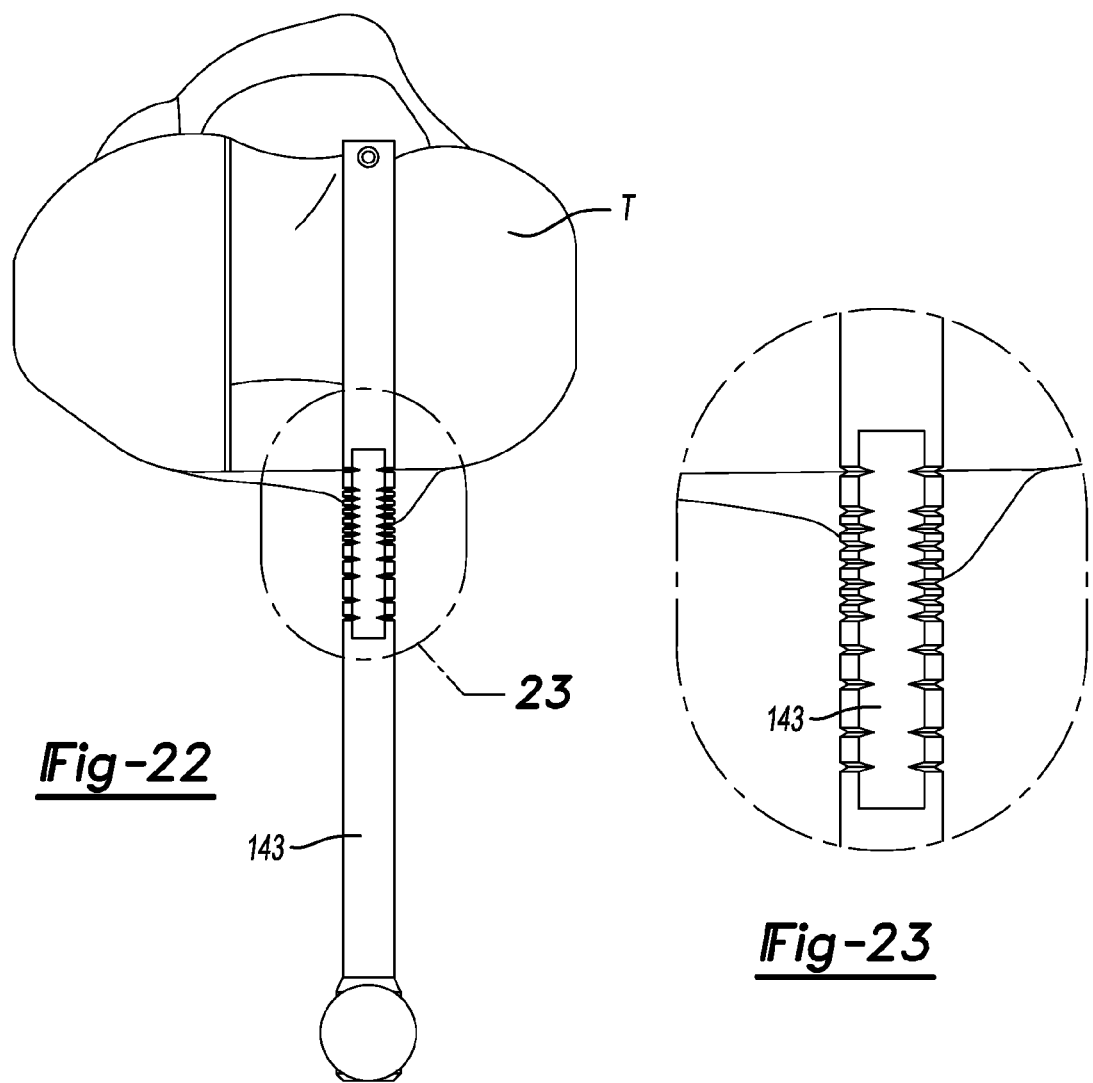
Fig-22
Fig-23

BI-CRUCIATE KNEE SYSTEM

CROSS-REFERENCE TO RELATED APPLICATIONS

This application is a continuation of U.S. patent application Ser. No. 13/470,630, filed on May 14, 2012, which claims the benefit of U.S. Provisional Application Nos. 61/486,023, filed on May 13, 2011 and 61/593,521, filed on Feb. 1, 2012. The entire disclosures of both of the above applications are incorporated herein by reference.

FIELD

The following disclosure recites generally to knee surgery and more specifically to instrumentation, implants, and related method for preparing a knee for a bi-cruciate knee implant.

SUMMARY

This section provides a general summary of the disclosure, and is not a comprehensive disclosure of its full scope or all of its features.

An instrument set for preparing a proximal tibia during a bi-cruciate retaining procedure can include a tibial resection block, a vertical cut guide, and a locking arm. The tibial resection block can be configured to be fixed to an anterior portion of the proximal tibia. The tibial resection block can define a slot that extends in a medial-lateral direction when the tibial resection block is fixed to the proximal tibia. The vertical cut guide can have a body, a medial arm, and a lateral arm. A medial cut slot can be defined between the body and the medial arm. A lateral cut slot can be defined between the body and the lateral arm. The cut guide can further comprise a tongue extending therefrom. The tongue can be configured to be received by and slidably translate along the slot of the tibial resection block. The locking arm can be coupled to the cut guide and be movable between an unlocked position and a locked position. In the unlocked position, the cut guide is permitted to translate relative to the tibial resection block. In the unlocked position, the locking arm can engage the tibial resection block and inhibit movement of the cut guide relative to the tibial resection block.

According to additional features, the locking arm can rotate relative to the cut guide between the unlocked and locked positions. The locking arm can comprise a finger that extends therefrom and that engages the tibial resection block in the locked position. The body of the cut guide can be open at the medial and lateral cut slots. The medial and lateral cut slots can terminate at partial bores that are configured to receive pins thereat. The body of the cut guide can have upper medial and lateral walls. The instrument set can further comprise an alignment guide having elongated arms configured to locate on opposite sides of the cut guide body. The instrument set can additionally comprise a tibial resection guide having a stylus configured to engage a lowest point of a medial tibial plateau.

A method for preparing a proximal tibia for receipt of a bi-cruciate implant can include determining a resection level of the proximal tibia. A tibial cut block can be fixed relative to the proximal tibia based on the determination. A vertical cut guide can slidably translate along a slot defined in the tibial cut block until a desired medial-lateral position relative to the proximal tibia has been attained. The vertical cut guide can be fixed relative to the tibial cut block based on attaining the desired medial-lateral position. A vertical medial cut can be prepared into the proximal tibia while referencing a medial slot defined in the vertical cut guide. A vertical lateral cut can be prepared into the proximal tibia while referencing a lateral slot defined in the vertical cut guide.

According to additional features, the method can further include locating a tongue extending from the vertical cut block into the slot of the tibial cut block. A locking arm extending from the vertical cut guide can be moved from an unlocked position to a locked position. In the locked position, a finger can extend from the arm that engages the tibial cut block. The locking arm can be rotated relative to the vertical cut guide from the unlocked position to the locked position. A medial side of the proximal tibia can be horizontally resected. A spacer can be positioned onto the resected medial side of the proximal tibia. A medial side gap can be verified. A lateral side of the proximal tibia can be horizontally resected. A spacer can be positioned onto the resected lateral side of the proximal tibia. A lateral side gap can then be verified. At least one pin can be advanced through a bore defined in the vertical cut guide and into the proximal tibia. The pin can be referenced during the preparation of the vertical, medial, and lateral cuts. The pin can inhibit undercutting of an ACL island.

According to other features, anterior tibial bone can be removed subsequent to preparing the horizontal medial and lateral side resections. The proximal tibia can be sized by locating a tibial template onto the proximal tibia. The tibial template can have a U-shaped body, a medial and lateral passage, and a medial and lateral cut guide. Anterior holes can be prepared into the tibia while referencing the medial and lateral drill guides on the tibial template. Keel holes can be prepared into the tibia while referencing the medial and lateral passages on the tibial template. A tibial tray trial insert connected to the tibial tray trial can be positioned onto the proximal tibia. Pegs extending from the trial insert can be located into the anterior holes. Keels extending from the trial insert can be located into the keel holes.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 1-37 illustrate tibial preparation according to one example of the present teachings.

FIG. 1 is a perspective view of an exemplary 4-in-1 cutting block shown with a selectively attachable ACL protector.

FIG. 2 is a perspective view of the 4-in-1 block of FIG. 1.

FIG. 3 is an anterior view of an exemplary tibia shown prior to performing tibial preparation.

FIG. 4 is an anterior view of the tibia of FIG. 3 and shown subsequent to the tibial preparation.

FIG. 5 is an anterior perspective view of the tibia shown with an extramedullary tibial resection guide attached thereto.

FIG. 6 is an anterior perspective view of the proximal tibia and shown with a tibial resection block coupled to the extramedullary tibial resection guide and located against the proximal tibia.

FIG. 7 is a medial perspective view of the proximal tibia of FIG. 8 shown with a terminal end of a modular stylus engaged to the lowest point of the medial tibial plateau.

FIG. 8 is an anterior perspective view of the proximal tibia shown with the modular stylus positioned with a terminal end of the modular stylus engaged to the lowest point of the medial tibial plateau.

FIG. 9 is an anterior perspective view of the proximal tibia of FIG. 8 shown with the tibial resection block coupled with a modular stylus being adjusted to a desired location.

FIG. 10 is an anterior perspective view of the proximal tibia shown with a vertical cut guide coupled to the tibial resection block in line with an ACL and tibial island.

FIG. 11 is an anterior view of the tibia of FIG. 10 and shown with the vertical cut guide coupled to the tibial resection block in a locked position.

FIG. 12 is an anterior view of the proximal tibia shown subsequent to performing a pair of vertical cuts that will form lateral and medial sides of an ACL island made while referencing the vertical cut guide.

FIG. 13 is a superior view of the proximal tibia shown with a pre-trial spacer located atop of the lateral plateau to verify the height of tibial bone that was resected.

FIG. 14 is an anterior perspective view of the proximal tibia and pre-trial spacer shown in FIG. 13.

FIG. 15 is a superior view of the proximal tibia shown with a Rongeur tool initially located for resection of the anterior portion of the tibia.

FIG. 16 is a close-up view of the anterior portion of the ACL island of FIG. 15.

FIG. 17 is an anterior perspective view of the proximal tibia of FIG. 15.

FIG. 18 is an anterior perspective view of the tibia of FIG. 17 and shown subsequent to resection of the anterior island and using a rasp to clean up the surface surrounding the ACL island.

FIG. 19 is an anterior perspective view of the proximal tibia shown with a tibial plateau angle gauge disposed thereon.

FIG. 20 is a close-up view of a scale of the tibial plateau angle gauge of FIG. 19.

FIG. 21 is a perspective view of a spacer tool used to verify a medial and lateral gap.

FIG. 22 is a superior view of the proximal tibia shown using an optional anterior/posterior sizer to verify tibia size.

FIG. 23 is a close-up view of a scale of the sizer shown in FIG. 22.

FIG. 24 is a perspective view of the proximal tibia and shown with a tibial template and anterior/posterior sizer disposed thereon used to verify size, rotation and slope.

FIG. 25 is a lateral view of the proximal tibia shown with the tibial template and anterior/posterior sizer of FIG. 24 disposed thereon.

FIG. 26 is an anterior perspective view of the proximal tibia and shown with the tibial template placed thereon and shown with a drill aligned for receipt by a medial anterior grill guide on the tibial template.

FIG. 27 is an exploded front perspective view of a tibial mask and tibial template.

FIG. 28 is an anterior perspective view of the proximal tibia and shown with a toothbrush keel blade aligned for receipt into a medial passage provided in the tibial template.

FIG. 29 is an anterior view of the proximal tibia of FIG. 28 and shown with the toothbrush keel blade received by the medial passage of the tibial template during formation of a medial groove in the tibia.

FIG. 30 is a front perspective view of a tibial tray trial and tibial tray trial insert constructed in accordance to one example of the present teachings.

FIG. 31 is a front perspective view of the tibial tray trial and tibial tray trial insert shown in an assembled position.

FIG. 32 is an anterior perspective view of the prepared proximal tibia shown with the tibial tray trial and tibial tray trial insert located thereon.

FIG. 33 is a medial perspective view of the proximal tibia and shown with a tibia bearing trial handle and tibial impactor coupled to the tibial tray trial.

FIG. 34 is an anterior perspective view of the proximal tibia of FIG. 33 and bearing trial handle tool.

FIG. 35 is an anterior perspective view of the proximal tibia of FIG. 34 shown with the bearing trial handle tool positioning a bearing onto the tibial tray.

FIG. 36 is a front perspective view of the proximal tibial of FIG. 35 shown with a medial and lateral bearing coupled to the tibial tray.

FIG. 37 is a front perspective view of the tibial tray of FIG. 36 shown with a femoral trial used to check range of motion.

Corresponding reference numerals indicate corresponding parts throughout the several views of the drawings.

DETAILED DESCRIPTION

Figure 1:
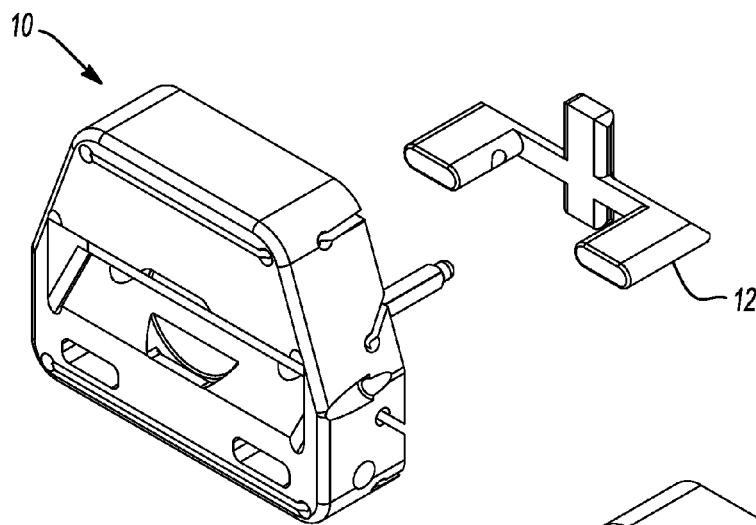

The following description will focus on preparation of a left knee for receipt of a bi-cruciate knee implant. In this regard, the following description will be directed toward various methods and techniques using instrumentation for preparing a left knee using a bi-cruciate knee system. It will be appreciated however, that the same may be adapted for use with a right knee.

While the intended focus of the instant application will be directed specifically to preparation of the tibia and related implants, a brief description of an exemplary preparation of a left femur will be described. In order to assess bone stock, potential ligament instability and the anatomical axis, a standing anterior/posterior x-ray may be used. In some examples, a 36 inch long standing anterior/posterior x-ray may be used. Initially, the angle between the anatomic and mechanical axis may be determined while assuring that the distal femoral cut is perpendicular to the mechanical axis. At this time, the femoral component size may be estimated pre-operatively by using lateral view x-rays and radio graphic templates. The appropriate size femoral component may be confirmed intra-operatively.

An intramedullary (IM) drill may be used to penetrate the intracondylar notch and dense cancellous bone of the distal femur to a depth of approximately 1.5-2 inches (3.5-5 centimeters). A 0.375 inch drill may be used to penetrate the distal femur. The canal entry location may be placed one centimeter above the insertion of the posterior cruciate ligament and slightly medial in the intracondylar notch. The appropriate left or right valgus wing may be chosen and slid onto the IM rod. The IM rod may be introduced into the femoral canal to de-pressurize the canal. The valgus wing may be slid until it rests against the medial distal condyle. The Slidex® Distal Resection Block and cut block adapter are both slid into the anterior holes of the valgus wing until the Slidex® Distal Resection Block contacts the anterior cortex of the femur.

To confirm the valgus angle, the alignment handle can be inserted into the cut block adapter and a ¼ inch alignment rod can be inserted and extended to the center of the femoral head. The Slidex® Distal Resection Block can then be pinned into place using ⅛ inch quick release drill pins in the most proximal pin holes of the block. The valgus wing can then be removed by removing the IM rod and pulling the valgus wing and cut block adapter distally away from the distal resection block leaving the Slidex® Distal Resection Block in place. Two resection slots of 0 or +3 mm are available for the distal resection. The 0 mm slot will resect 9 mm from the most prominent part of the medial distal condyle. If additional distal resection is required, the +3 mm slot will resect 12 mm. If additional distal resection is required beyond the +3 mm slot, the resection guide can be shifted proximally by utilizing the +2 or +4 mm ⅛ inch pin holes. A 0.054 inch saw blade can be used to complete the distal resection through the selected slot. The resected distal femur can be checked by using a flat instrument. The bone surface may be re-cut or filed as necessary to ensure proper resection. For additional stability, the femoral block handle can be utilized.

An exemplary method of femoral sizing will now be described. Initially, the adjustable anterior/posterior sizer may be placed against the resected distal surface with the feet in contact with the posterior condyles of the femur. In a first option, fixed rotation feet may be used. In another option, adjustable rotation feet may be used. An adjustable dial can be used with the anterior/posterior sizer. The adjustable rotation feet are available in left and right varieties with the ability to set an external rotation from 0 to 10 degrees. In one example, it is recommended that an initial setting of 3 degrees of rotation be utilized. The femoral component size can now be read from the central scale. If the size indicated is in between standard sizing or a larger flexion gap is desired, a choice may be made to choose the smaller size and shift the femoral 4-in-1 block placement anteriorly. In order to shift the component anteriorly, a screw mechanism in the central portion of the sizer is turned which raises the level of drill holes in one millimeter increments. A scale is located on the sizer to indicate how far the component will be anteriorly shifted. If medial/lateral width is a concern, the appropriately sized medial/lateral width checker can be inserted into the anterior/posterior sizer to further evaluate the proper size of the femur. Next, two 4-in-1 cutting block location holes are drilled utilizing a ⅛ inch drill pin. In one example, the final medial/lateral position of the femoral component is not determined during this step, but is addressed later in the technique.

Figure 2:
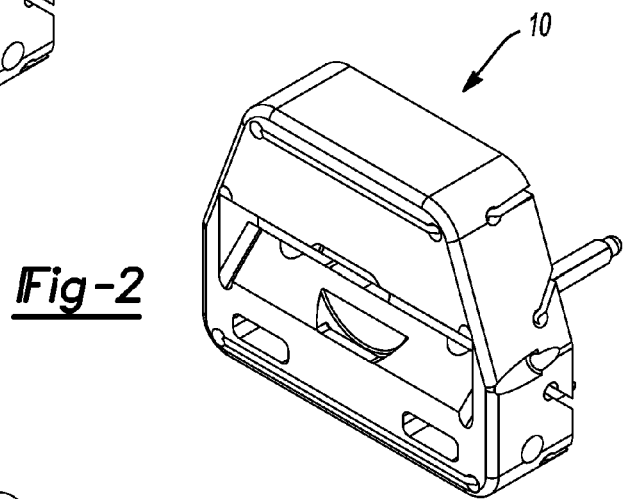

With initial reference now to FIGS. 1 and 2, initial preparation of the distal femur using a 4-in-1 block 10 according to the present teachings will be described. At the outset, a surgeon may choose the desired 4-in-1 block 10 that matches the selected size on the anterior/posterior sizer and place it into the ⅛ inch holes drilled into the distal femur. A 0.054 inch feeler blade can be used to determine the amount of anterior bone resection. If the feeler blade indicates a probability of notching, an anterior/posterior femoral shift block may be used to adjust the cut block holes anteriorly in one millimeter increments. Notably, moving the block anteriorly will resect additional posterior condylar bone. ⅛ inch pins can be placed in the side holes provided on the femoral 4-in-1 block 10. The anterior/posterior block must be sitting flush against the distal femur at this point. An ACL protector 12 may be secured into place relative to the 4-in-1 block 10. The ACL protector 12 can be used to block the blade from inadvertently cutting the ACL. Once the position of the 4-in-1 block 10 is satisfactory, a surgeon can resect the anterior and posterior bone, and the anterior and posterior chamfers using a 0.054 inch saw blade. Again, care must be taken not to cut the ACL while making the posterior and posterior chamfer boney resections.

Figure 3:
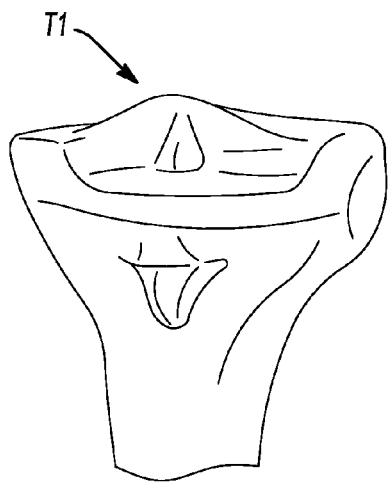
Figure 4:
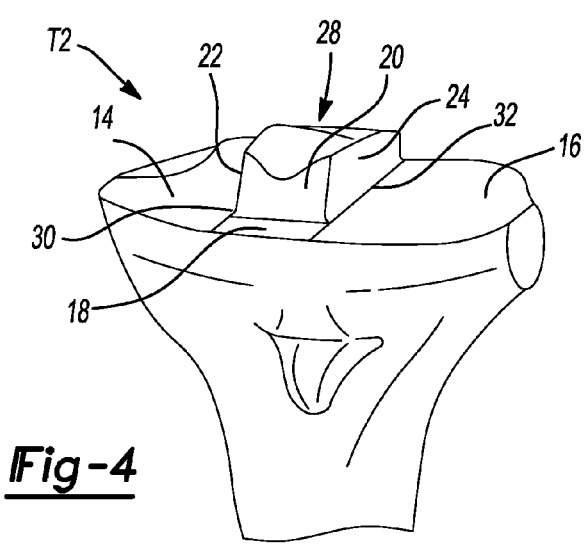
Figures 5, 6:
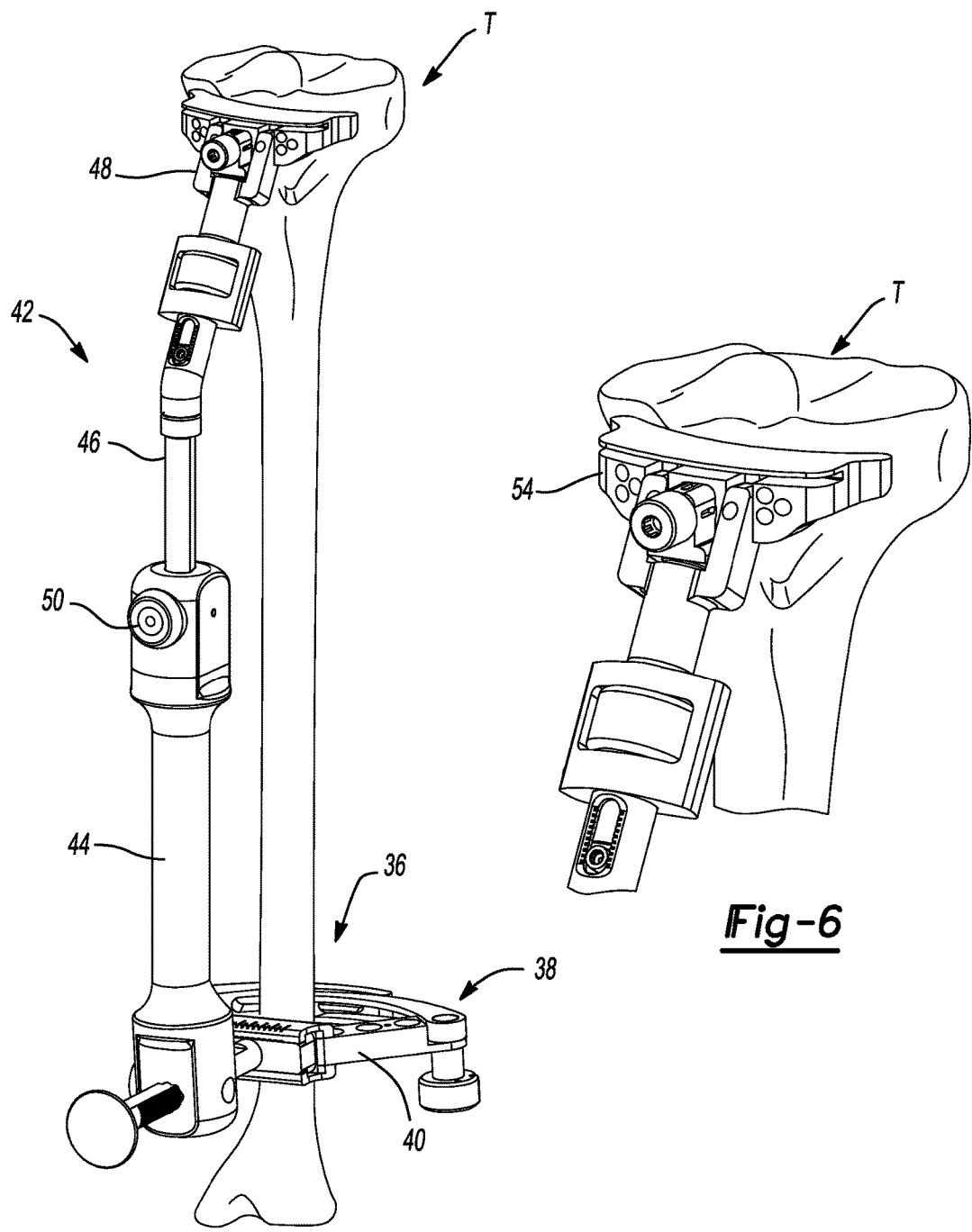
Figure 7:
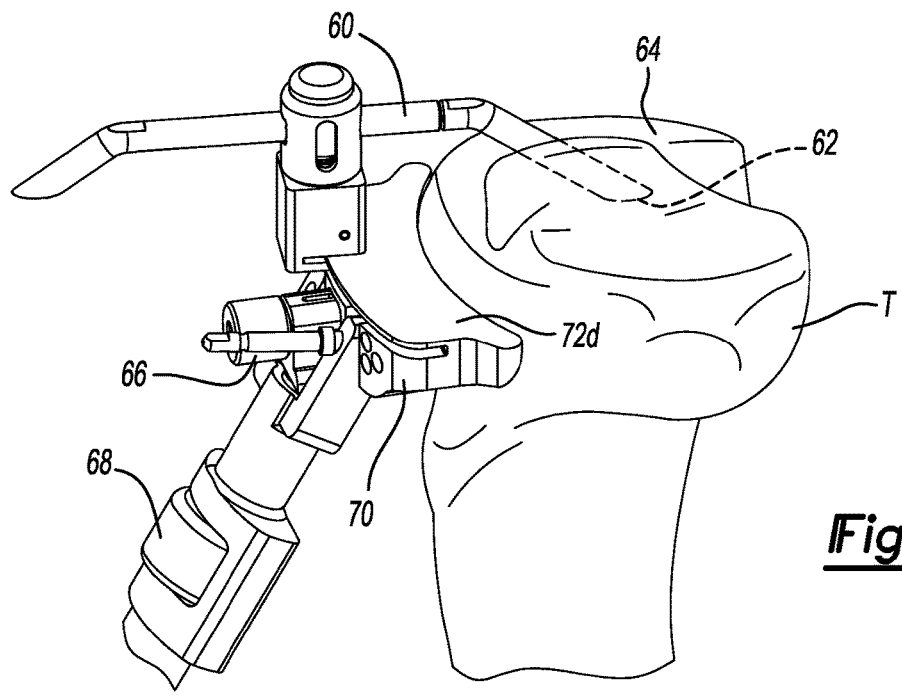
Figure 8:
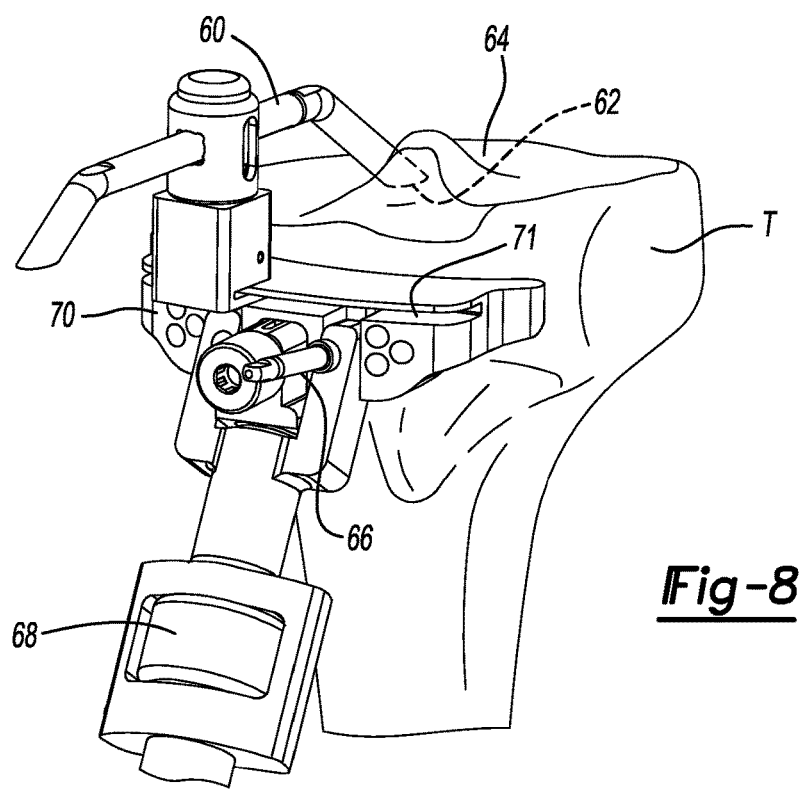

With reference now to FIGS. 3-37, preparation of a proximal tibia for a bi-cruciate knee system according to a first example will be described. FIG. 3 illustrates a tibia T1 prior to performing the instant surgical technique. FIG. 4 illustrates a tibia T2 subsequent to performing the tibial technique according to the present teachings. Of note, the tibia T2 includes a medial plateau 14, lateral plateau 16, anterior plateau 18, anterior chamfer wall 20, medial vertical wall 22, and lateral vertical wall 24. The anterior chamfer wall 20, the medial vertical wall 22, and the lateral vertical wall 24 can collectively cooperate to form an ACL island 28. A radius 30 is formed at a transition between the medial plateau 14 and the medial vertical wall 22. Similarly, a radius 32 is formed at a transition between the lateral plateau 16 and the lateral vertical wall 24.

With reference now to FIGS. 5-29, resection of the tibia T will be described. With the knee flexed, spring loaded arms 36 and 38 of an ankle clamp 40 are located around the distal tibia T just around the malleoli. The ankle clamp 40 can generally be attached to an extramedullary tibial resection guide 42. The extramedullary tibial resection guide 42 can further comprise a handle portion 44, a telescoping rod portion 46, and a resection block connecting portion 48. A button 50 can be provided on the extramedullary tibial resection guide 42 that can control telescoping action of the rod portion 46 generally from the handle portion 44.

Figure 9:
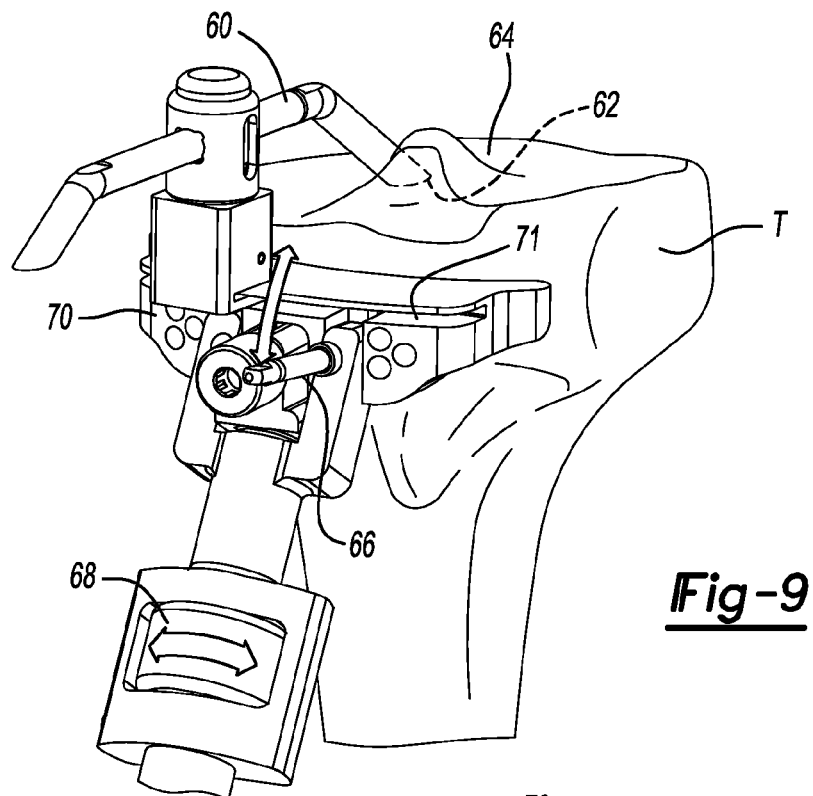

At this point, a tibial resection block 54 (FIG. 6) can be placed against the proximal tibia T. Returning now to FIG. 5, from the sagittal view, the side of the extramedullary tibial resection guide 42 is adjusted such that it is generally parallel with the shaft of the tibia T. The tibial resection block is set at 4 degrees of slope (other measurements may be used) when attached to the extramedullary guide. Once adjustment of the resector axis is correct in the medial/lateral view, the resection block connecting portion 48 is rotated until the shaft of the resector is just medial to the tibial tubercle. Using a stylus 60 (FIGS. 7 and 8), the extramedullary tibial resection guide 42 is adjusted such that a terminal end 62 of the stylus 60 is engaged to a lowest point of the medial tibial plateau 64. Using a ⅛ inch pin 66, the extramedullary tibial resection guide 42 is secured to the tibia T. A dial 68 may be used to fine tune the resection level prior to making any cut (FIG. 9).

Figure 10:
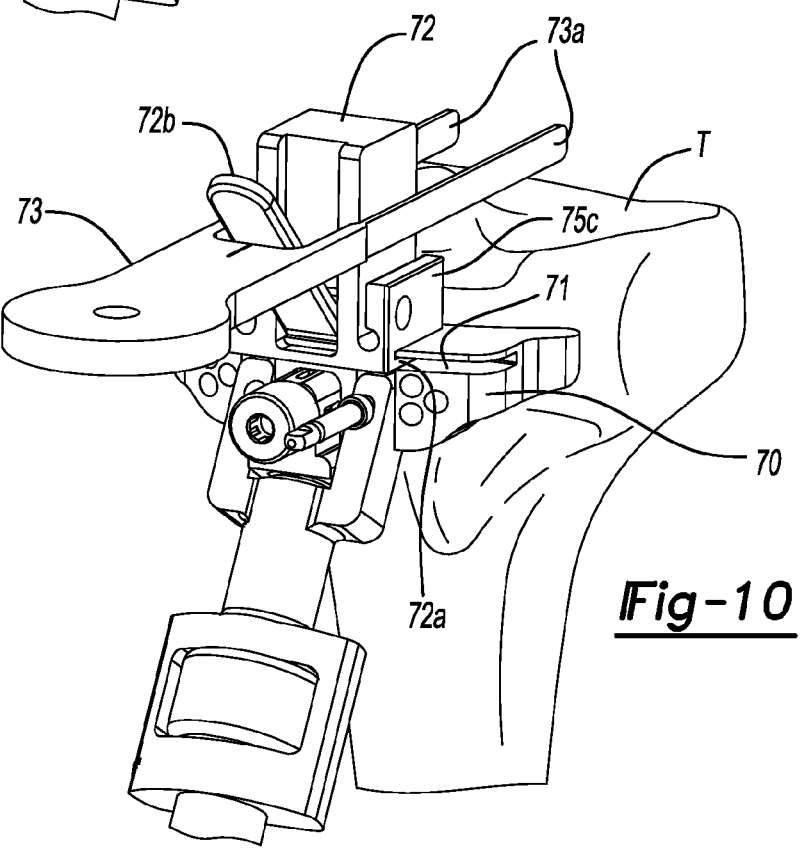
Figure 11:
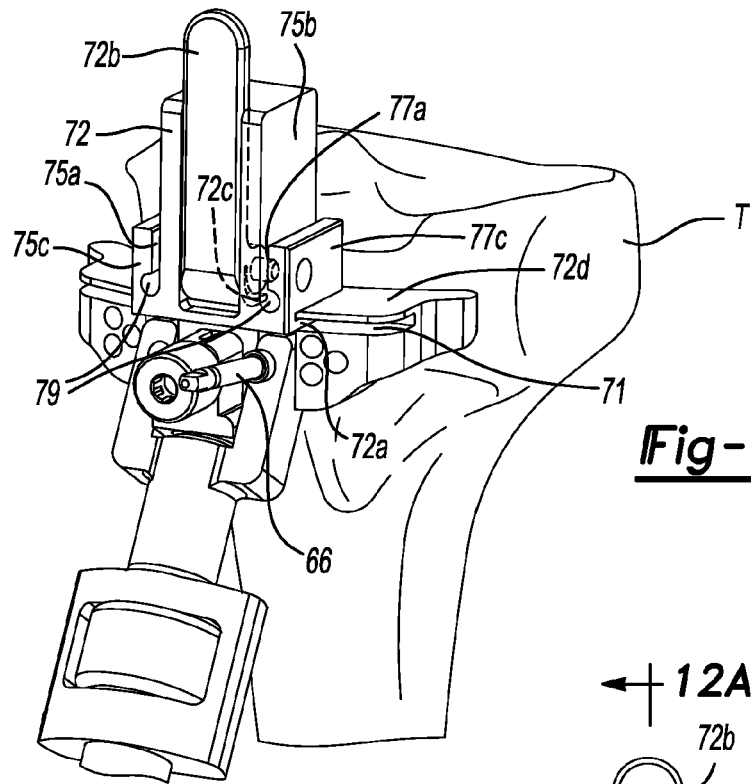
Figure 12:
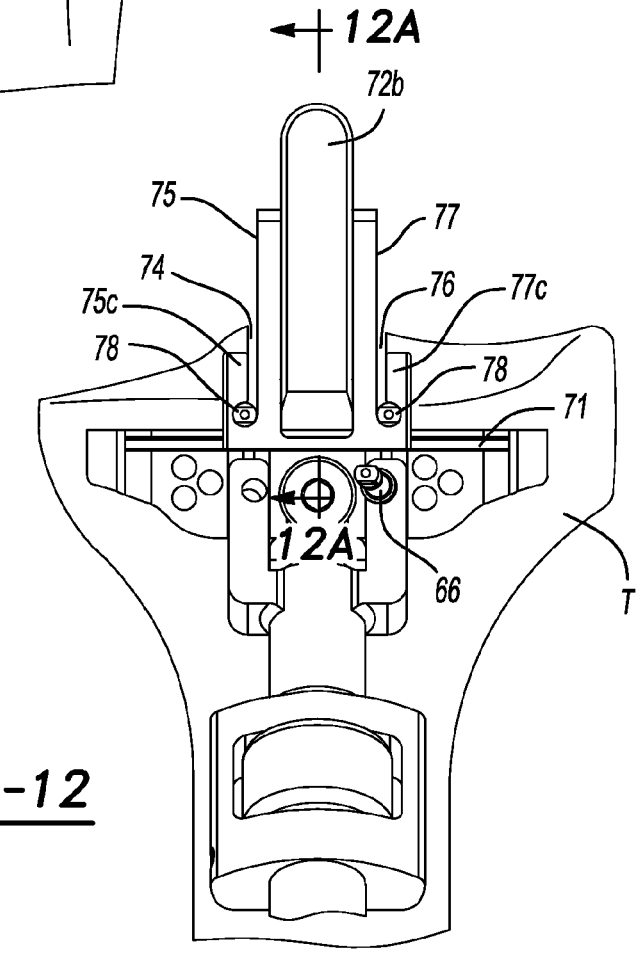

Of note, the stylus 60 is set for a 4 mm resection. Prior to pinning the extramedullary tibial resection guide 42 in place, make sure to allow for adjustability of the height of a tibial resection cut block 70. The tibial resection block 70 can define a horizontal slot 71. Once the resection level is set, the stylus 60 can be removed. A vertical cut guide 72 can then be attached to the tibial resection block 70 (FIG. 10).

The vertical cut guide 72 can then be adjusted to an appropriate position (in a medial/lateral direction along the slot 71) to make the desired vertical cuts. Specifically, a tongue 72a extending from the vertical cut guide 72 can slide along the slot 71. An alignment guide 73 can be used to aid in the positioning of the vertical cut guide 72. The alignment guide 73 generally includes a pair of parallel and elongated arms 73a that slidably locate on opposite sides of the vertical cut guide 72. Of note, the vertical cuts will determine the final tibial component rotation. It is important to leave equal amounts of bone on the medial and lateral aspect of the ACL fibers. At this point, the vertical cut guide 72 can be clamped in place by rotating a locking arm 72b from an unlocked position shown in FIG. 10 to a locked position shown in FIGS. 11 and 12. In one example, the locking arm 72b can have a finger 72c that rotates into fixed engagement with an upper surface 72d of the cut block 70. With a reciprocating saw, a vertical medial cut 74 can be prepared while passing a saw through a medial slot 75a defined between a main body 75b of the vertical cut guide 72 and a medial arm 75c. The vertical medial cut 74 may be prepared while referencing a medial surface 75 of the vertical cut guide 72. It will be appreciated that the vertical medial cut 74 may be prepared while concurrently referencing the medial arm 75c. After the vertical medial cut 74 has been prepared, the vertical lateral cut may be made. The vertical lateral cut 76 can be prepared while passing a saw through a lateral slot 77a defined between the main body 75b of the vertical cut guide 72 and a lateral arm 77c. The vertical lateral cut 76 may be prepared while referencing a lateral surface 77 of the vertical cut guide 72. It will be appreciated that the vertical lateral cut 76 may be prepared while concurrently referencing the lateral arm 77c. Headless vertical pins 78 can be located through partial bores 79 (FIGS. 11 and 12) provided in the vertical cut guide 72 driven into the anterior tibia T. The vertical medial cut 74 and the vertical lateral cut 76 can both be prepared using a saw blade having teeth or cutting structure consistent for forming the radius cuts 30 and 32 identified in FIG. 4. Notably, by incorporating a radius at this transition, the bone at the transition between the respective medial and lateral plateaus 14, 16 and ACL island 28 (FIG. 4) can be stronger as compared to a transverse, 90 degree intersecting cut. Next, the vertical cut guide 72 is removed from the headless vertical pins 78. The medial side of the tibia T may then be horizontally resected.

With reference to FIG. 12A, a cross-sectional view of the cut guide 72 is shown. FIGS. 12B and 12C show an alternate vertical cut guide 72'. Unless otherwise described herein, the cut guide 72' incorporates similar features as the cut guide 72 that are identified with like reference numerals having a prime suffix. The cut guide 72' provides a captured vertical medial slot 75a' and a captured vertical lateral slot 77a'. Specifically, an upper medial wall 80 and an upper lateral wall 82 close the respective vertical medial slot 75a' and the vertical lateral slot 77a'. The upper medial and lateral walls 80 and 82 can assist in maintaining a saw blade within the respective medial and lateral slots 75a' and 77a'.

Figure 13:
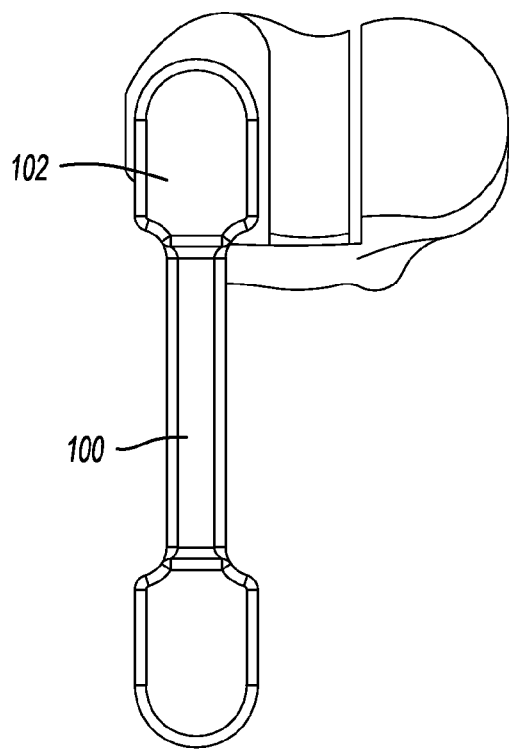
Figure 14:
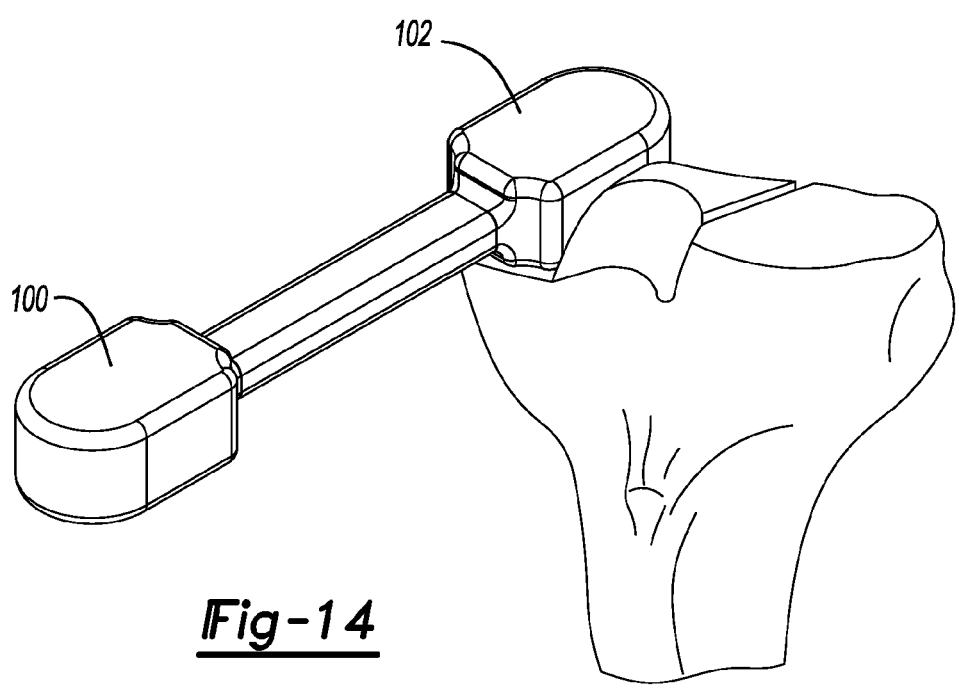

At this point, the medial side gap may be verified in extension using an 8/9 mm spacer block 100 (FIGS. 13-14). If the 9 mm spacer portion 102 is too tight, additional tibial bone will need to be removed. This can be done by simply dialing the resection block down 1 mm. Once the medial side extension gap is adequate, the lateral side of the tibia T is horizontally resected with the headless vertical pins 78 left in place. The headless vertical pins 78 protect against undercutting the ACL island 28.

Figure 15:
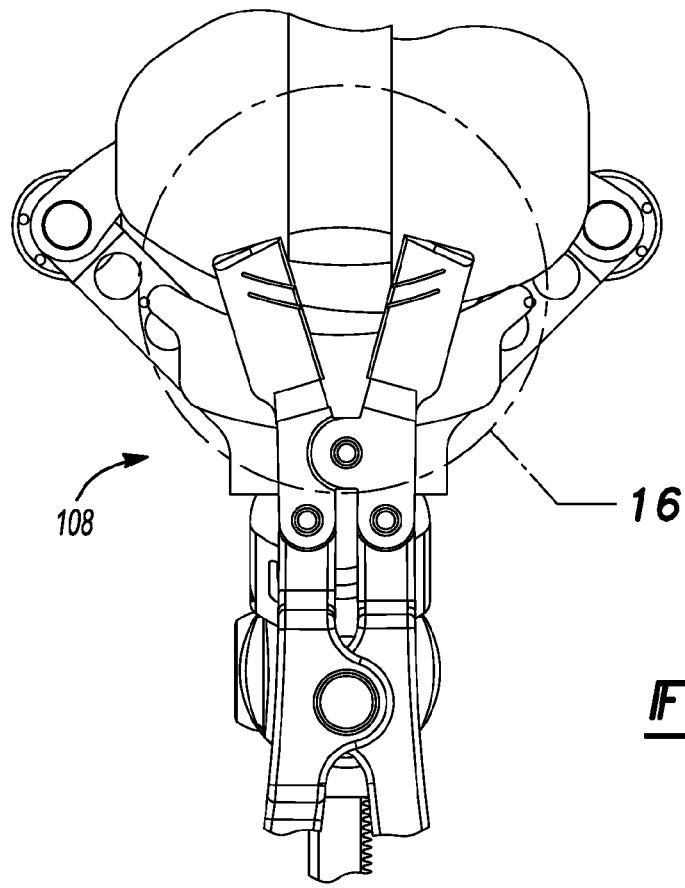
Figure 16:
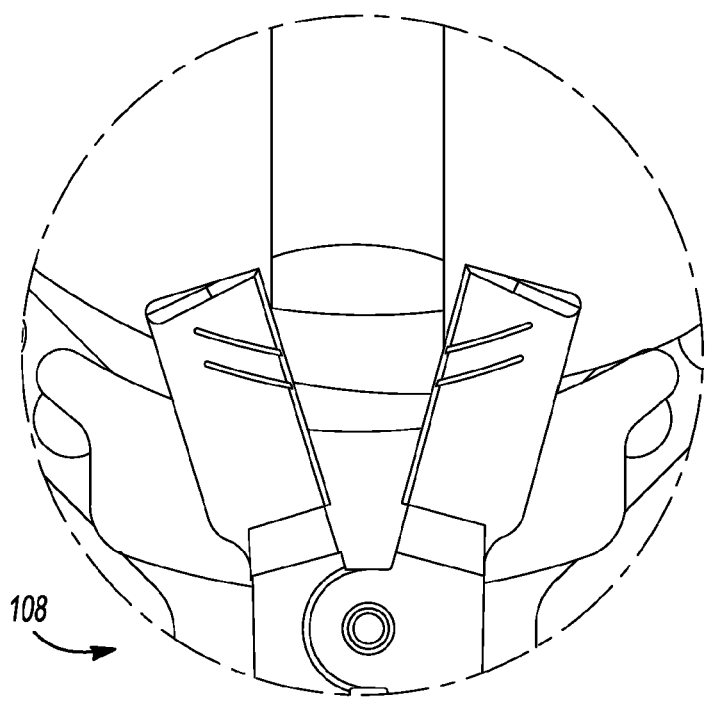
Figure 17:
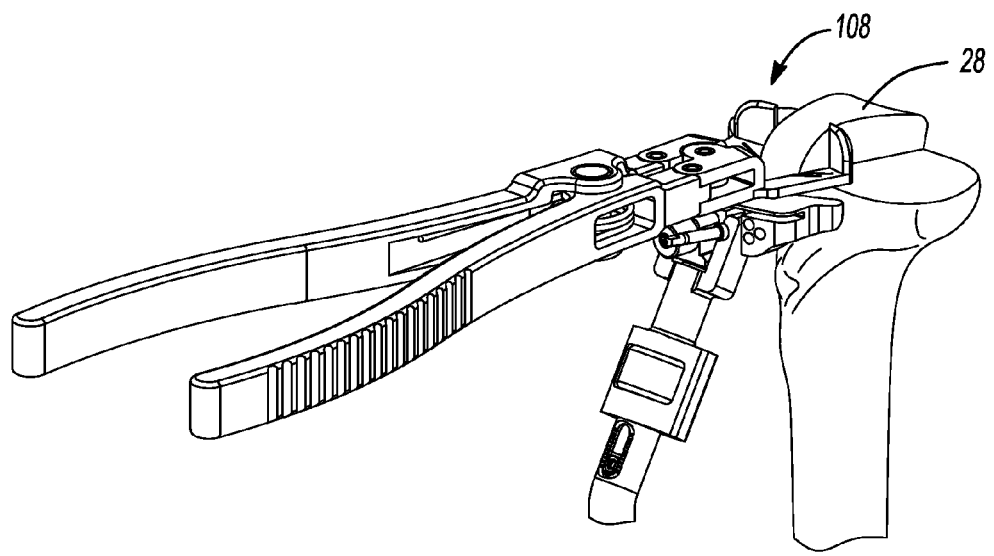
Figure 18:
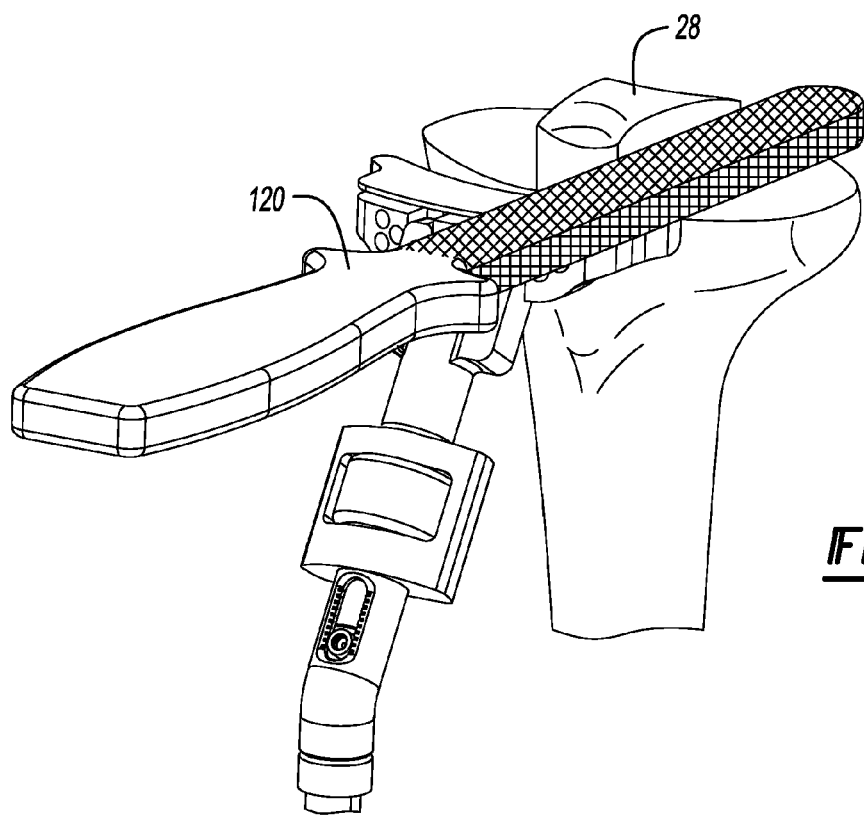
Figure 19:
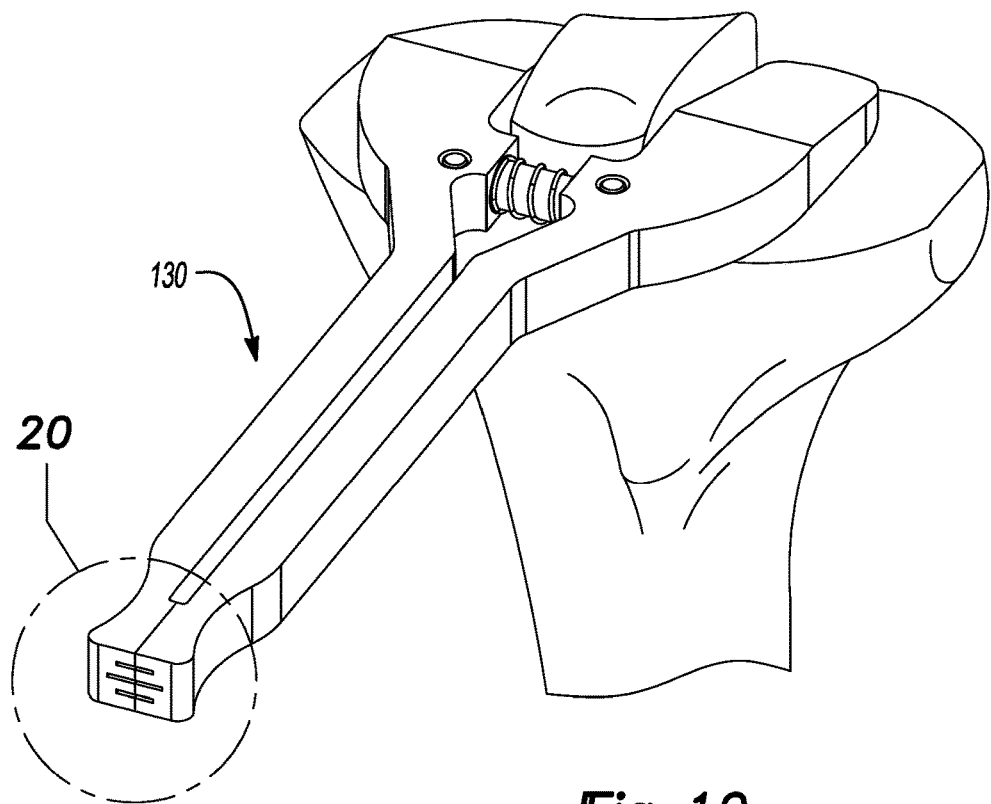
Figure 20:
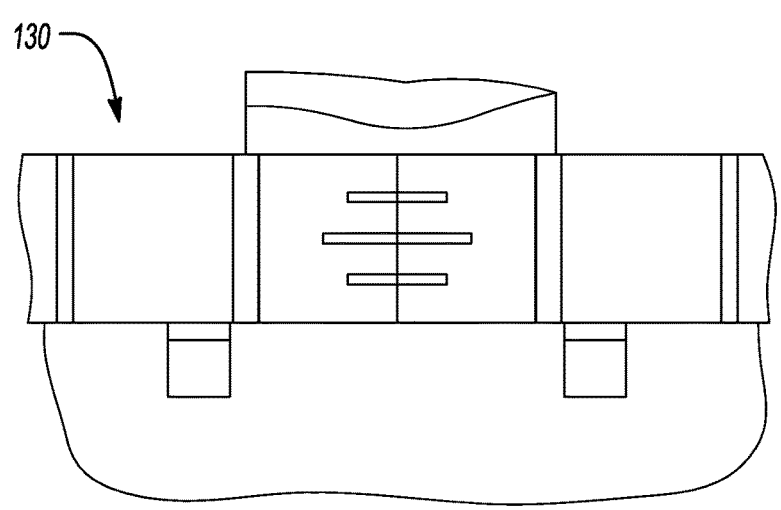

As illustrated in FIGS. 15-17, a Rongeur tool 108 can be used to remove the anterior bone making sure to round the corners of the anterior island. Next, an ACL island rasp 120 (FIG. 18) is used to clean the resected tibia T to ensure that there are no rough edges around the ACL island 28 and respective medial and lateral plateaus 14 and 16. Using the tibial plateau angle gauge 130 (FIG. 19), the tibial slope cuts are verified to have an equal amount of slope. This will be important for the tibial base plate to be secured properly, and for the proper wear and function of the system.

Turning now to FIG. 21, tibial sizing for an intact and functional ACL will be described. The medial and lateral gaps are verified using a spacer tool 140. A series of 1 mm spacers 142 may be magnetically coupled as needed. Rotation and slope may also be verified. Optionally, the tibia T may be sized with an anterior/posterior sizer 143 (FIGS. 22 and 23).

Figure 24:
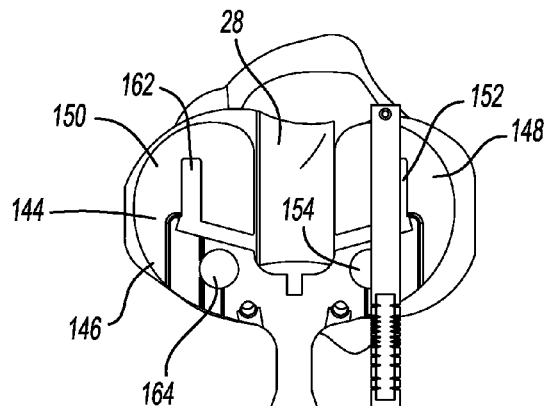
Figure 25:
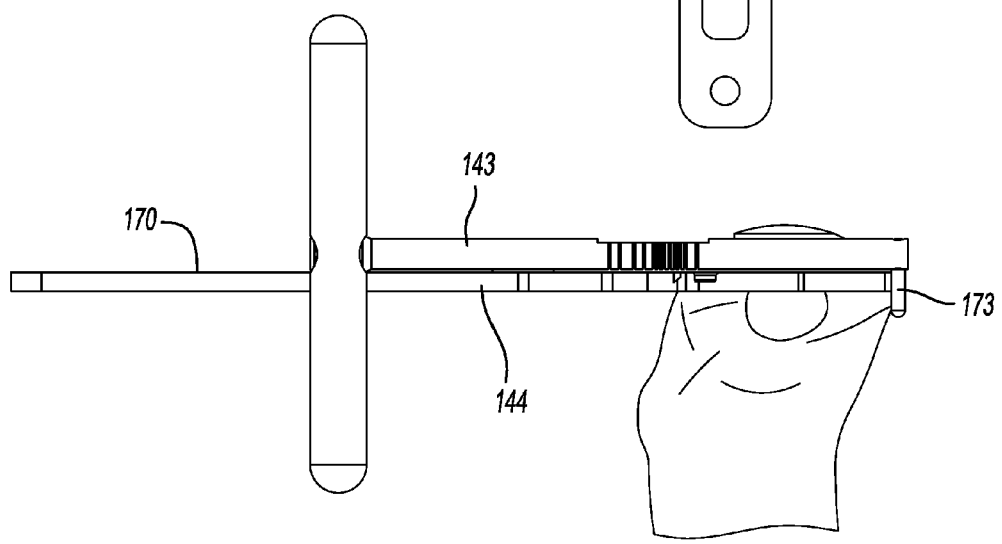

The tibia T may then be sized with a tibial template 144 (FIGS. 24-25). The tibial template 144 generally comprises a U-shaped body portion 146 having a lateral side 148, and a medial side 150. A lateral passage 152 and a lateral anterior drill guide 154 can be provided on the lateral side 148. Similarly, a medial passage 162 and medial anterior drill guide 164 can be provided on the medial side 150. Because rotation is determined by the position of the ACL island 28, it is important to check for accurate rotation. Base rotation can be made relative to the tibial tubercle and the malleolar axis. At this point, an extramedullary alignment check can be made by placing a ¼ inch alignment rod through a handle 170 of the tibial template 144. Slight external rotation is preferred to optimize patellofemoral tracking. Once the final rotation has been determined, the position can be marked by extending anterior marks of the tibial template 144 onto the anterior tibia such as by electrocautery. A locator pin 173 extending from the anterior/posterior sizer 143 can be located around the posterior edge of the tibia T. Extra caution should be used to avoid internal rotation of the tibial template 144 due to the presence of lateral soft tissue.

Figure 26:
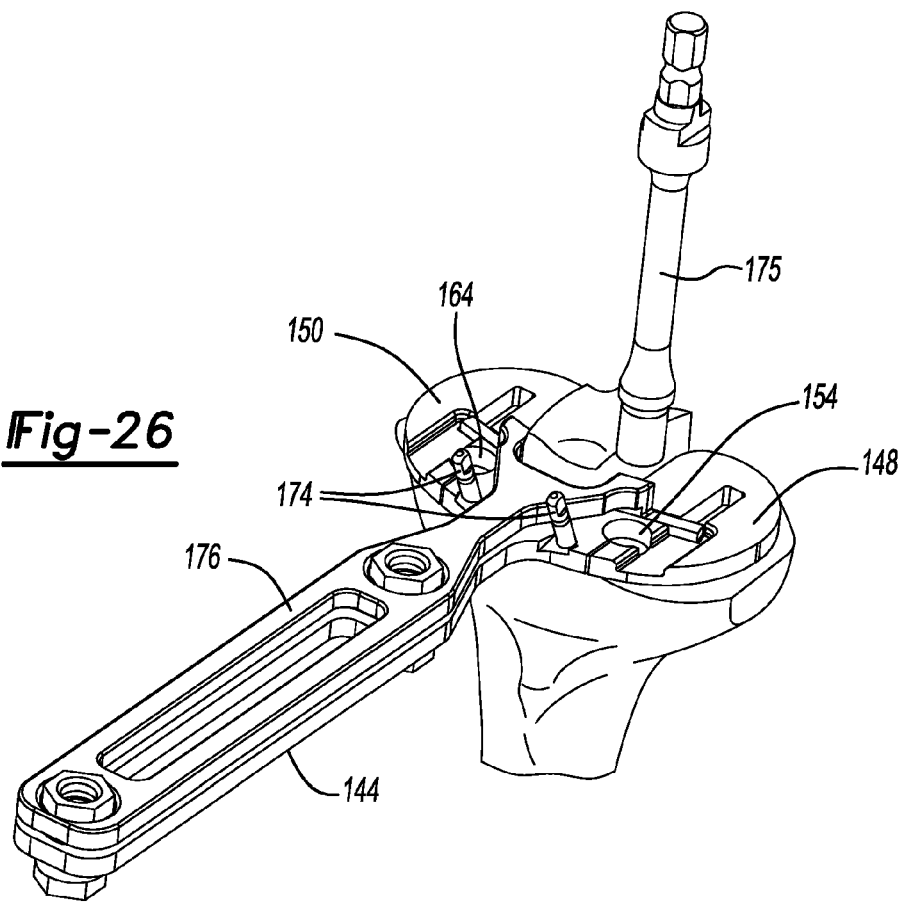
Figure 27:
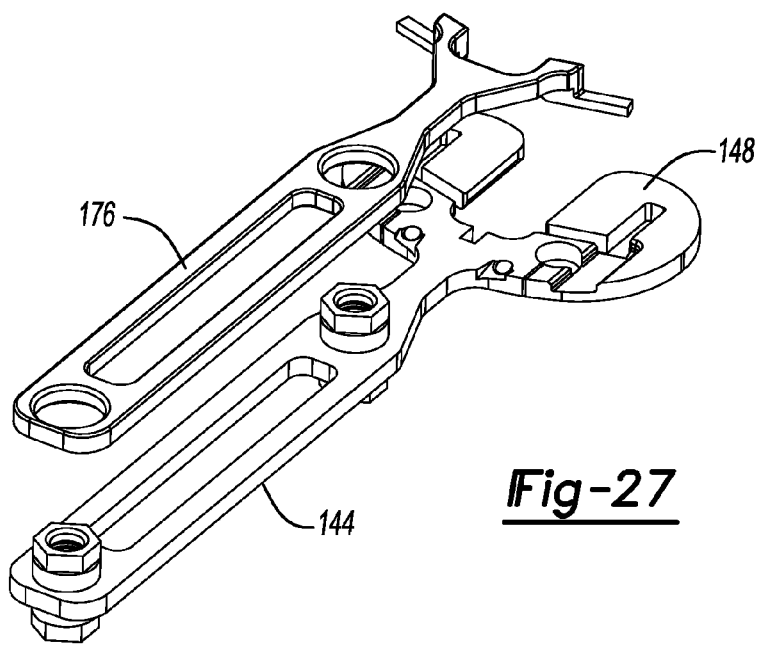

Tibial preparation for an intact and functional ACL will now be described. With the tibial template 144 in proper position (FIG. 26), such as by way of pins 174, a drill 175 can be used to prepare an anterior hole while referencing the lateral anterior drill guide 154. A tibial mask 176 may be coupled to the tibial template 144. In one example, a ⅛ inch drill 175 may be used (FIG. 26). Next, another anterior hole can be drilled with the drill 175 while referencing the medial anterior drill guide 164.

Figure 28:
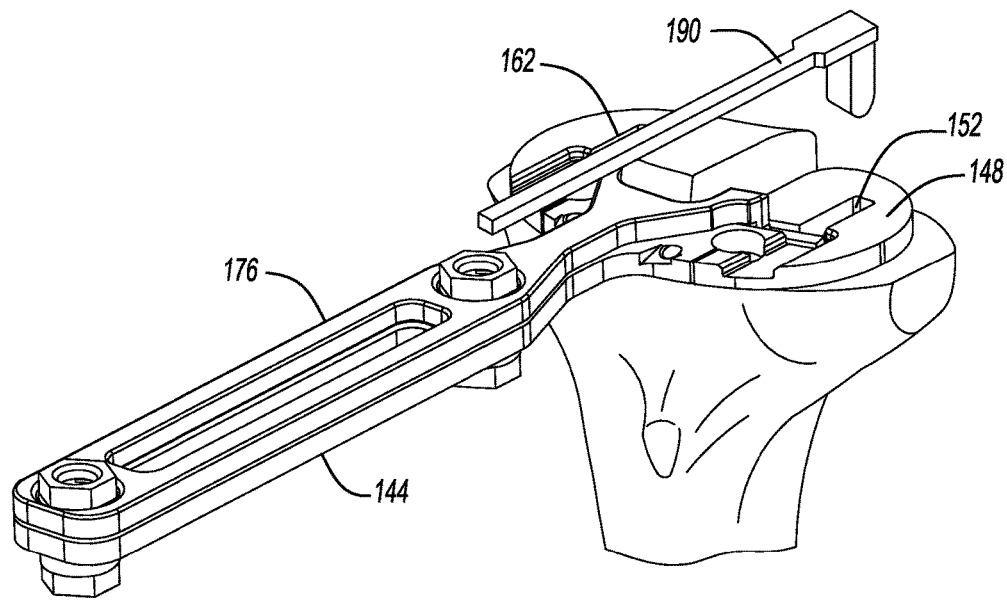
Figure 29:
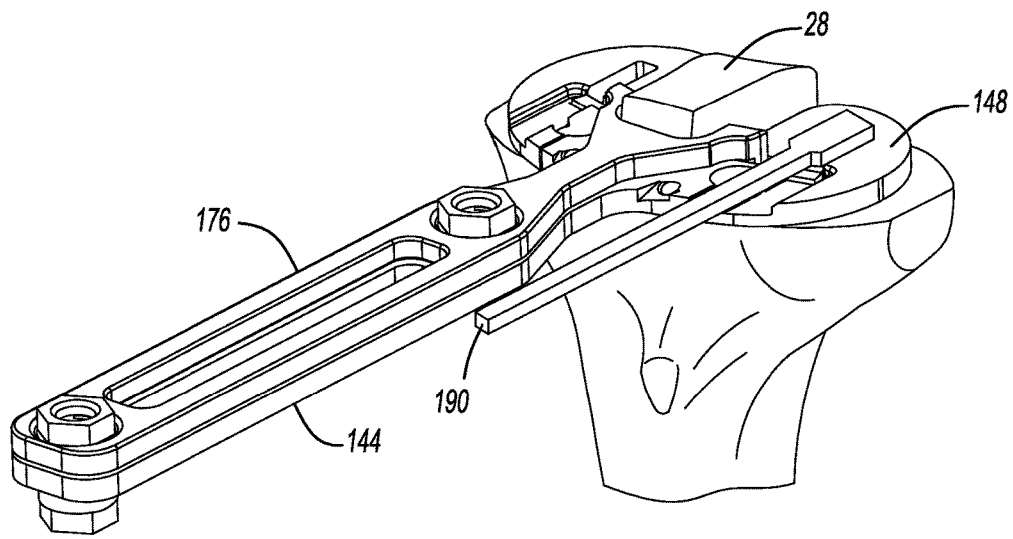
Figure 30:
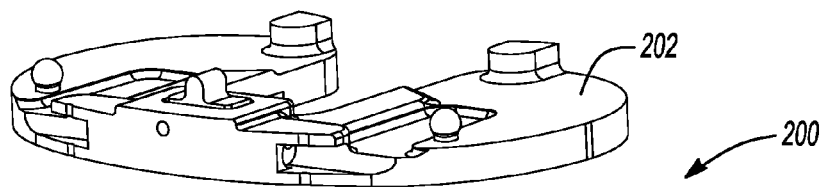
Figure 31:
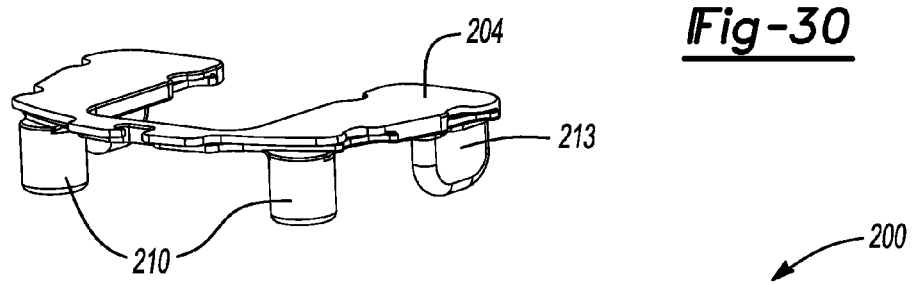
Figure 32:
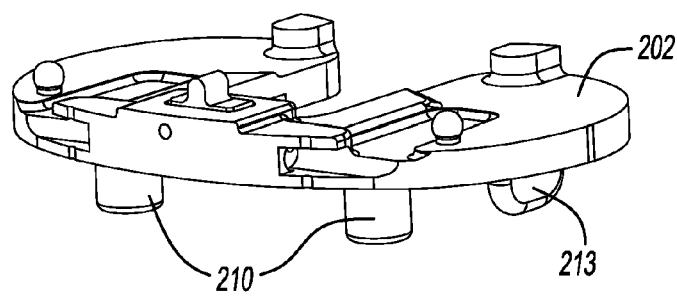
Figure 32:
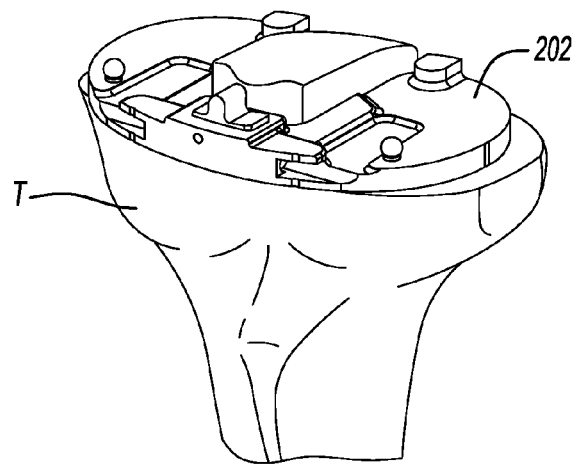
Figures 33, 34:
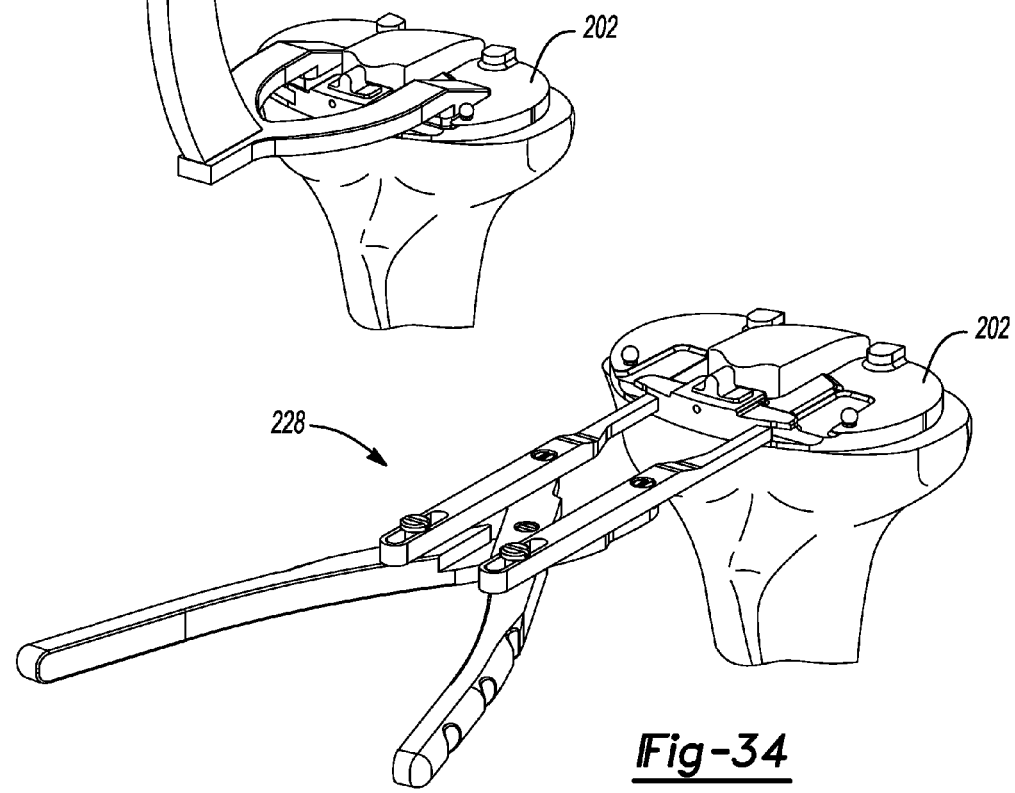
Figure 35:
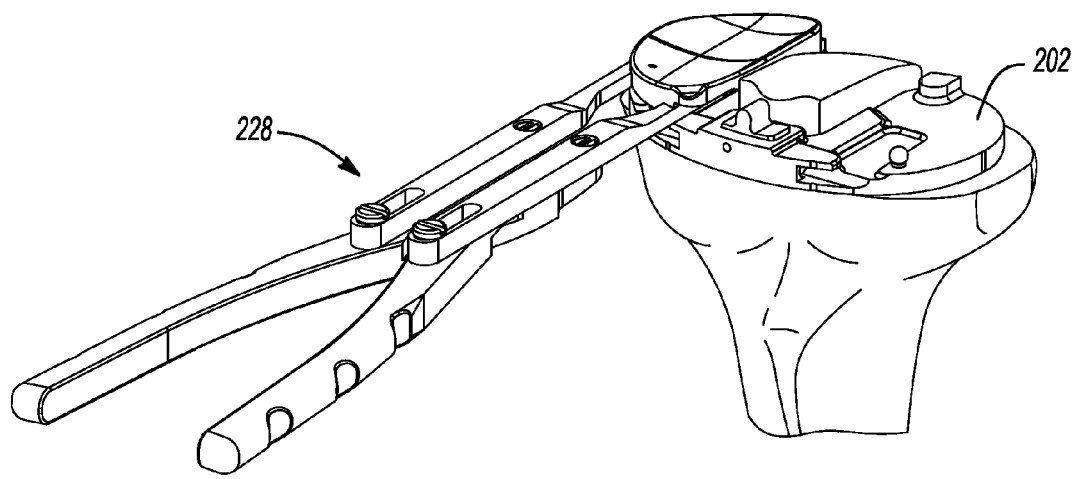
Figure 36:
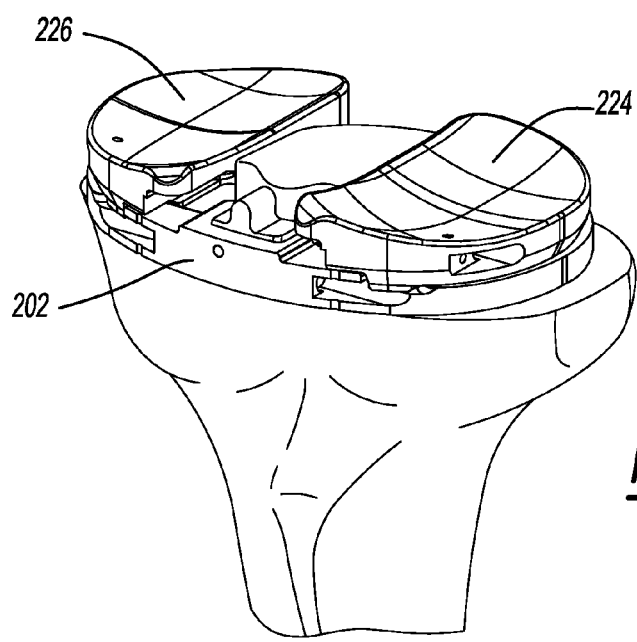
Figure 37:
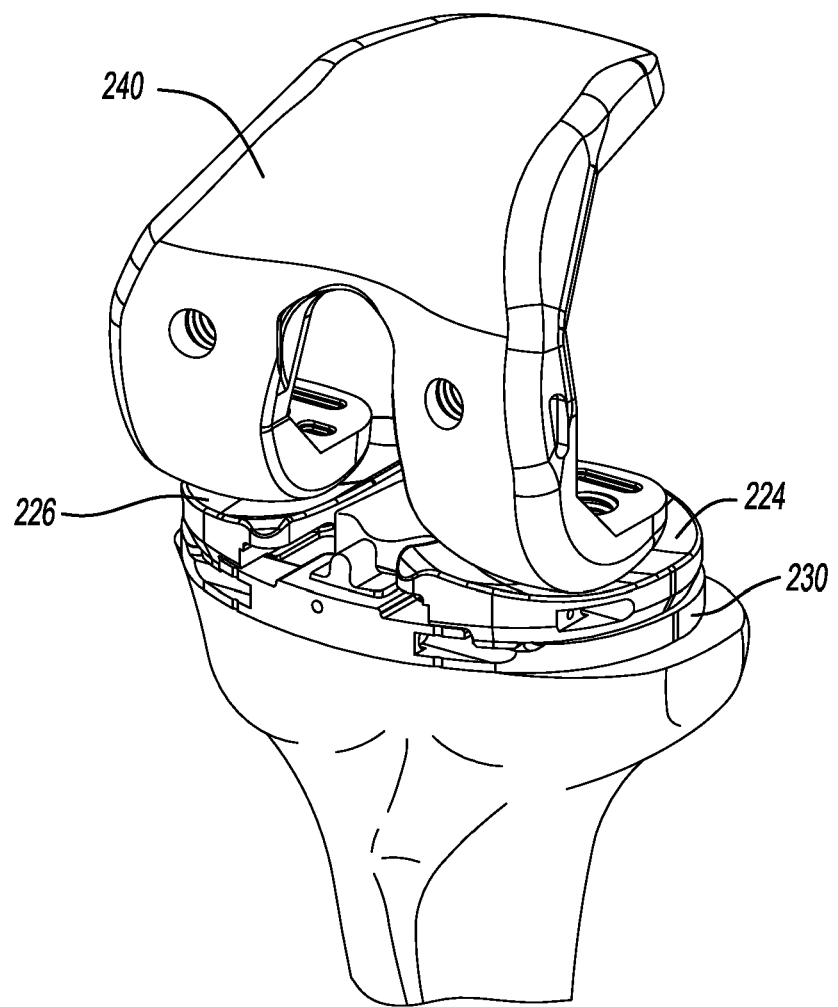

With the tibial template 144 secured in place, a toothbrush keel blade 190 can be used to prepare both the medial and lateral tibia for the keeled base plate. Specifically, the toothbrush keel blade 190 can be inserted through the lateral passage 152 and the medial passage 162 (FIGS. 28 and 29). While the tibia T is being prepared, the tibial trial assembly 200 (FIGS. 30 and 31) can be prepared. The tibial trial assembly 200 can include a tibial tray trial 202 and tibial tray trial insert 204. Once tibial preparation is complete, the tibial template 144 can be removed from the proximal tibia. The tibial tray trial 202 can have multiple versions that provide various dimensions. Similarly, the tibial tray trial insert 204 can also provide various dimensions suitable for the needs of a particular patient. Of note, the tibial tray trial insert 204 includes pegs 210 and keels 213. The pegs 210 have a spacing that corresponds to the passages made earlier with the drill 175. Similarly, the keels 213 have dimensions suitable for insertion into the grooves prepared with the toothbrush keel blade 190. As illustrated in FIG. 33, a tibial tray trial 202 is shown being impacted onto the tibia T using a tibial impactor 232. As illustrated in FIGS. 34-36, a lateral tibial bearing trial 224 and a medial tibial bearing trial 226 can be coupled to the tibial tray trial 202 using a bearing trial handle tool 228 and trialed. Also, the tibial tray trial 202 can be positioned with the bearing trial handle tool 228 (FIG. 34). As shown in FIG. 37, a femoral trial 240 can be used to verify range of motion.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An instrument set for preparing a proximal tibia during a bi-cruciate retaining procedure, the instrument set comprising:
   a tibial resection block configured to be fixed to an anterior portion of the proximal tibia, the tibial resection block defining a first slot that continuously extends in a medial-lateral direction from a lateral portion of the proximal tibia to a medial portion of the proximal tibia when the tibial resection block is fixed to the proximal tibia, the first slot configured to act as a guide for performing a proximal resection of both the medial portion and the lateral portion of the proximal tibia;
   a vertical cut guide configured to be received in and to slidably translate along the first slot of the tibial resection block in the medial-lateral direction, the vertical cut guide configured to define both a medial slot for performing a first sagittal resection of the medial portion of the proximal tibia and a lateral slot for performing a second sagittal resection of the lateral portion of the proximal tibia; and
   a gauge having a first portion configured to be positioned on the medial portion and a second portion configured to be positioned on the lateral portion of the proximal tibia after the performing of the proximal resection, wherein the gauge has indicia to determine if a slope of the medial portion differs from a slope of the lateral portion.

2. The instrument set of claim 1, wherein the vertical cut guide is configured such that the medial and lateral cut slots are open at a proximal surface of the vertical cut guide.

3. The instrument set of claim 1, wherein the vertical cut guide is configured such that the medial and lateral cut slots are each at least partially closed by a wall at a proximal surface of the vertical cut guide.

4. The instrument set of claim 1, wherein the medial and lateral cut slots terminate at partial bores that are configured to receive pins therein.

5. The instrument set of claim 4, wherein the pins act to inhibit undercutting of an ACL island during the first sagittal resection and the second sagittal resection.

6. The instrument set of claim 1, further comprising an alignment guide with elongated arms that are configured to be slidably located in the medial and lateral cut slots, the alignment guide configured to aid in the positioning of the vertical cut guide relative to the medial portion and the lateral portion of the proximal tibia.

7. The instrument set of claim 1, further comprising a tibial resection guide configured to couple to the vertical cut guide and rotate relative thereto, the tibial resection guide having a stylus configured to engage a lowest point of a medial tibial plateau.

8. The instrument set of claim 1, further comprising a locking arm coupled to the cut guide at a location between the medial and lateral cut slots, the locking arm movable between an unlocked position where the vertical cut guide is permitted to translate within the first slot and a locked position where the locking arm engages the tibial resection block and inhibits movement of the vertical cut guide relative to the tibial resection block.

9. The instrument set of claim 1, wherein the vertical cut guide is configured to be adjustable relative to the tibial resection block and is configured with a body to space the medial and lateral cut slots relative one another to set a location for the first and second sagittal resections that form an anterior cruciate ligament island in the proximal tibia.

10. An instrument set for preparing a proximal tibia during a bi-cruciate retaining procedure, the instrument set comprising:
    a tibial resection block configured to be fixed to an anterior portion of the proximal tibia, the tibial resection block defining a first slot that continuously extends in a medial-lateral direction from a lateral portion of the proximal tibia to a medial portion of the proximal tibia when the tibial resection block is fixed to the proximal tibia, the first slot configured act as a guide for performing a proximal resection of both the medial portion and the lateral portion of the proximal tibia;
    a vertical cut guide configured to be received in and to slidably translate along the first slot of the tibial resection block in the medial-lateral direction, the vertical cut guide defining a bore that communicates with a sagittal slot defined by the vertical cut guide;
    a tibial tray trial having a U-shaped body portion with a lateral side and a medial side, the tibial tray trial configured to receive an island on a proximal tibia to preserve an anterior cruciate ligament of the patient;
    a tibial tray trial insert configured to be coupled to the tibial tray trial, wherein the tibial tray trial insert has a medial portion configured to be positioned on the medial portion of the proximal tibia after the performing of the proximal resection and has a lateral portion configured to be positioned on the lateral portion of the proximal tibia after the performing of the proximal resection, wherein the tibial tray trial insert has at least one of a peg or keel configured to insert into one prepared recesses in the proximal tibia; and
    a lateral tibial bearing trial and a medial tibial bearing trial configured to couple to the tibial tray trial, the lateral tibial bearing trial configured to couple to the lateral side of the tibial tray trial and be disposed lateral of the island when assembled and the medial tibial bearing trial configured to couple to the medial side of the tibial tray trial and be disposed medial of the island when assembled.

11. The instrument set of claim 10, wherein the sagittal slot comprises both a medial slot for performing a first sagittal resection of the medial portion of the proximal tibia and a lateral slot for performing a second sagittal resection of the lateral portion of the proximal tibia.

12. The instrument set of claim 11, wherein the bore comprises a partial bore configured to receive a pin therein, the pin configured to fix the vertical cut guide to the proximal tibia at one or both of the medial portion and the lateral portion thereof.

13. The instrument set of claim 12, wherein the pin acts to inhibit undercutting of the island during at least a first sagittal resection using the sagittal slot as a guide.

14. The instrument set of claim 10, wherein the vertical cut guide is configured such that the sagittal slot is open at a proximal surface of the vertical cut guide.

15. The instrument set of claim 10, wherein the vertical cut guide is configured such that the sagittal slot is at least partially closed by a wall at a proximal surface of the vertical cut guide.

16. An instrument set for preparing a proximal tibia during a bi-cruciate retaining procedure, the instrument set comprising:
- a tibial resection block configured to be fixed to an anterior portion of the proximal tibia, the tibial resection block defining a first slot that continuously extends in a medial-lateral direction from a lateral portion of the proximal tibia to a medial portion of the proximal tibia when the tibial resection block is fixed to the proximal tibia, the first slot configured act as a guide for performing a proximal resection of both the medial portion and the lateral portion of the proximal tibia;
- a vertical cut guide configured to be received in and to slidably translate along the first slot of the tibial resection block in the medial-lateral direction, the vertical cut guide defining a bore that communicates with a sagittal slot defined by the vertical cut guide, wherein the bore comprises a partial bore configured to receive a pin therein, the pin configured to fix the vertical cut guide to the proximal tibia at one or both of the medial portion and the lateral portion thereof;
- a tibial template configured to size the tibia, wherein the template has a handle and a U-shaped body portion with a medial side configured to be positioned on the medial portion of the proximal tibia after the performing of the proximal resection and a lateral side configured to be positioned on the lateral portion of the proximal tibia after the performing of the proximal resection, wherein the tibial template forms one or more of a drill guide and a passage therein; and
- an anterior/posterior sizer having a locator pin extending from a posterior end portion thereof wherein the anterior/posterior sizer is configured to position the locator pin at a posterior edge of the tibia and has indicia along an anterior portion thereof.

17. The instrument set of claim 16, wherein the pin acts to inhibit undercutting of an ACL island during at least a first sagittal resection using the vertical cut guide.

18. The instrument set of claim 16, wherein the vertical cut guide is configured such that the sagittal slot is open at a proximal surface of the vertical cut guide.

19. The instrument set of claim 16, wherein the vertical cut guide is configured such that the sagittal slot is at least partially closed by a wall at a proximal surface of the vertical cut guide.

* * * * *

UNITED STATES PATENT AND TRADEMARK OFFICE
CERTIFICATE OF CORRECTION

PATENT NO. : 10,485,555 B2
APPLICATION NO. : 14/876142
DATED : November 26, 2019
INVENTOR(S) : Metzger et al.

Page 1 of 1

It is certified that error appears in the above-identified patent and that said Letters Patent is hereby corrected as shown below:

In the Claims

In Column 10, Line 38, in Claim 10, after "one", insert --or more-- (Second Occurrence)

In Column 11, Line 1, in Claim 16, delete "instn ment" and insert --instrument-- therefor In Column 12, Line 9, in Claim 16, delete "thereof" and insert --thereof,-- therefor Signed and Sealed this
Fourth Day of August, 2020

Andrei Iancu
*Director of the United States Patent and Trademark Office*